United States Patent
Iwao et al.

(10) Patent No.: US 11,286,261 B2
(45) Date of Patent: Mar. 29, 2022

(54) FOURTH-GENERATION EGFR TYROSINE KINASE INHIBITOR

(71) Applicants: NAGASAKI UNIVERSITY, Nagasaki (JP); IWATE MEDICAL UNIVERSITY, Iwate (JP); JAPANESE FOUNDATION FOR CANCER RESEARCH, Tokyo (JP)

(72) Inventors: Masatomo Iwao, Nagasaki (JP); Tsutomu Fukuda, Nagasaki (JP); Fumito Ishibashi, Nagasaki (JP); Yoshimasa Uehara, Iwate (JP); Naoyuki Nishiya, Iwate (JP); Yusuke Oku, Iwate (JP); Shingo Dan, Tokyo (JP); Takao Yamori, Tokyo (JP)

(73) Assignees: NAGASAKI UNIVERSITY, Nagasaki (JP); IWATE MEDICAL UNIVERSITY, Iwate (JP); JAPANESE FOUNDATION FOR CANCER RESEARCH, Tokyo (JP)

(*) Notice: Subject to any disclaimer, the term of this patent is extended or adjusted under 35 U.S.C. 154(b) by 109 days.

(21) Appl. No.: 16/497,917

(22) PCT Filed: Mar. 29, 2018

(86) PCT No.: PCT/JP2018/013370
§ 371 (c)(1),
(2) Date: Sep. 26, 2019

(87) PCT Pub. No.: WO2018/181777
PCT Pub. Date: Oct. 4, 2018

(65) Prior Publication Data
US 2021/0122759 A1     Apr. 29, 2021

(30) Foreign Application Priority Data
Mar. 29, 2017 (JP) .............................. JP2017-064866

(51) Int. Cl.
*C07D 491/147* (2006.01)
(52) U.S. Cl.
CPC .................. *C07D 491/147* (2013.01)
(58) Field of Classification Search
CPC ................................................. C07D 491/147
See application file for complete search history.

(56) References Cited

FOREIGN PATENT DOCUMENTS

WO     2004/014917 A2     2/2004

OTHER PUBLICATIONS

Registry No. 2190501-94-9, File Registry on STN, Mar. 13, 2018.*

Cross et al., AZD9291, an Irreversible EGFR TKI, Overcomes T790M-mediated Resistance to EGFR Inhibitors in Lung Cancer, Cancer Discovery, 4(9):1047-1061 (2014).
Ercan at al., EGFR Mutations and Resistance to Irreversible Pyrimidine-Based EGFR Inhibitors, Clin. Cancer Res., 21(17):3913-3923 (2015).
FDA News Release, "FDA approves new pill to treat certain patients with non-small cell lung cancer", Nov. 13, 2015 Available at http://www.fda.gov/NewsEvents/Newsroom/PressAnnouncements/ucm472525.htm, 3 pages.
Fujikawa at al., Total synthesis of lamellarins D, L, and N, Tetrahedron, 62(4):594-604 (2006).
Fukuda et al., Design, Synthesis, and Evaluation of A-ring-modified Lamellarin N Analogues as Noncovalent Inhibitors of the EGFR T790M/L858R Mutant, Bioorg. Med. Chem., 25(24):6563-6580 (2017).
International Preliminary Report on Patentability for Corresponding International Application No. PCT/JP2018/013370, dated Sep. 3, 2018, 7 pages (4 pages of English Translation and 3 pages of Original Document).
International Search Report and Written Opinion for Corresponding International Application No. PCT/JP2018/013370, dated May 15, 2018, 9 pages (2 pages of English Translation and 7 pages of Original Document).
Jia et al., Overcoming EGFR(T790M) and EGFR(C797S) resistance with mutant-selective allosteric inhibitors, Nature, 534:129-132 (2016).
Kim et al., The EGFR T790M Mutation in Acquired Resistance to an Irreversible Second-Generation EGFR Inhibitor, Mol. Cancer Ther., 11(3):784-791 (2012).
Li et al., BIBW2992, an Irreversible EGFR/HER2 Inhibitor Highly Effective in Preclinical Lung Cancer Models, Oncogene, 27:4702-4711 (2008).
Ploypradith et al., Total Synthesis of Natural and Unnatural Lamellarins with Saturated and Unsaturated D-Rings, J. Org. Chem., 71(25):9440-9448 (2006).
Sharma et al., Epidermal Growth Factor Receptor Mutations in Lung Cancer, Nat. Rev. Cancer, 7:169-181 (2007).
Tangdenpaisal et al., Designing New Analogs for Streamlining the Structure of Cytotoxic Lamellarin Natural Products, Chem. Asian J., 10(4):925-937 (2015).
Theppawong et al., Facile and Divergent Synthesis of Lamellarins and Lactam-Containing Derivatives With Improved Drug Likeness and Biological Activities, Chem. Asian. J., 10(12):2631-2650 (2015).
Thress et al., Acquired EGFR C797S mutation mediates resistance to AZD9291 in non-small cell lung cancer harboring EGFR T790M, Nat. Med., 21:560-564 (2015).

(Continued)

*Primary Examiner* — Rebecca L Anderson
(74) *Attorney, Agent, or Firm* — Marshall, Gerstein & Borun LLP

(57) ABSTRACT

Provided is a compound having a tyrosine kinase inhibitory activity specific to C797S resistant mutant EGFR (particularly C797S tertiary-resistant mutant EGFR) and is useful as a C797S resistant mutant EGFR (particularly C797S mutant tertiary-resistant EGFR) specific tyrosine kinase inhibitor, an agent for preventing and/or treating non-small cell lung cancer with resistance mutant EGFR and the like, and the like.

6 Claims, 4 Drawing Sheets

(56) References Cited

OTHER PUBLICATIONS

Walter et al., Discovery of a Mutant-Selective Covalent Inhibitor of EGFR That Overcomes T790M-mediated Resistance in NSCLC, Cancer Discov., 3(12):1404-1415 (2013).
Yoshida et al., Synthesis, Resolution, and Biological Evaluation of Atropisomeric (aR)- And (aS)-16-methyllamellarins N: Unique Effects of the Axial Chirality on the Selectivity of Protein Kinases Inhibition, J. Med. Chem., 56(18):7289-7301 (2013).
Yu et al., Acquired Resistance of EGFR-Mutant Lung Cancer to a T790M-Specific EGFR Inhibitor: Emergence of a Third Mutation (C797S) in the EGFR Tyrosine Kinase Domain, JAMA Oncol., 1(7):982-984 (2015).
Zhou et al., Novel Mutant-Selective EGFR Kinase Inhibitors Against EGFR T790M, Nature, 462:1070-1074 (2009).

\* cited by examiner (a) All view (b) ATP binding pocket (c) Electrostatic potential map

FOURTH-GENERATION EGFR TYROSINE KINASE INHIBITOR

TECHNICAL FIELD

The present invention relates to a compound having an EGFR tyrosine kinase inhibitory activity and an EGFR tyrosine kinase inhibitor containing the compound.

BACKGROUND ART

80% of lung cancer is non-small cell lung cancer, and gene mutation of epidermal growth factor receptor (EGFR) is observed in 20-30% of the non-small cell lung cancer. The major mutation is the L858R mutation or exon 19 deletion in the EGFR kinase domain. This mutation constantly activates transmission of cell proliferation signal from EGFR to the nucleus and causes canceration of the cells. Tyrosine kinase inhibitors (first-generation EGFR-TKI) such as Gefitinib (1) and Erlotinib (2) show remarkable antitumor effects for non-small cell lung cancer having such activating mutation EGFR (L858R or exon 19 deletion). On the other hand, if these drugs are continuously used, secondary-resistant mutation (T790M) occurs in EGFR in about one year in many cases and cancer relapses (non-patent document 1). To deal with this resistant mutation, an irreversible inhibitor Afatinib (3) (second-generation EGFR-TKI) in which Michael receptor is incorporated into the skeleton of Gefitinib (1) was developed (non-patent document 2). However, this drug strongly inhibits not only T790M secondary-resistant mutant EGFR but also wild-type EGFR (WT) which is present in normal cells. Therefore, the blood concentration of the drug cannot be sufficiently increased, and a sufficient therapeutic effect has not been shown for non-small cell lung cancer having resistant mutant EGFR (non-patent document 3).

On the other hand, as a third-generation EGFR-TKI having selective inhibitory activity against T790M secondary-resistant mutant EGFR, irreversible inhibitors such as WZ4002 (4) having a pyrimidine skeleton (non-patent document 4), Rociletinib (CO-1686) (5) having a pyrimidine skeleton (non-patent document 5), and Osimertinib (AZD9291) (6) having a pyrimidine skeleton (non-patent document 6) were recently developed. Among these, 6 which was developed by AstraZeneca was subject to accelerated examination as a breakthrough therapeutic drug by the US FDA, and was approved as a therapeutic drug for EGFR-T790 M positive mutation non-small cell lung cancer in November 2015 (non-patent document 7). In Japan, the clinical use of 6 has become possible since May 2016.

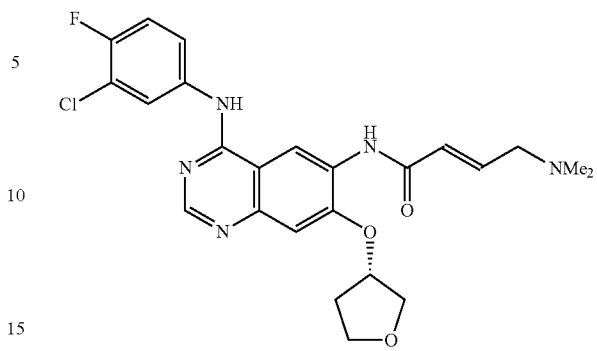

Afatinib (3)

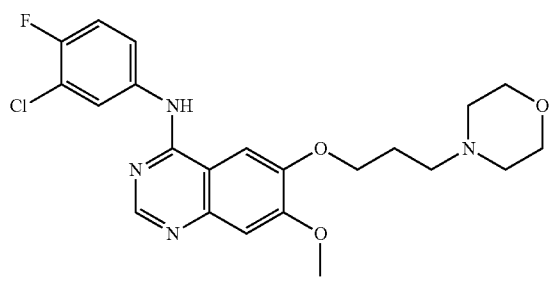

Gefitinib (1)

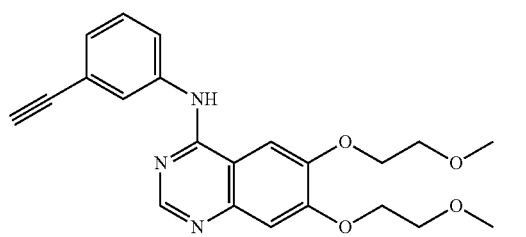

Erlotinib (2)

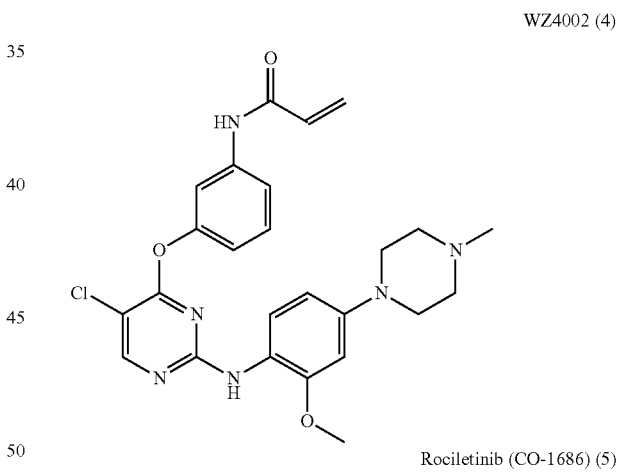

WZ4002 (4)

Rociletinib (CO-1686) (5)

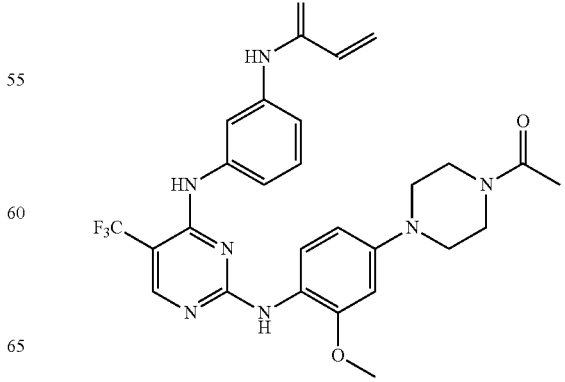

-continued

Osimertinib (AZD9291) (6)

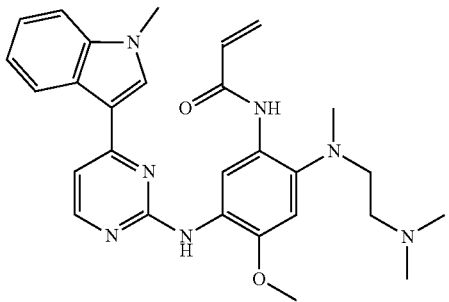

However, a new C797S tertiary-resistant mutant EGFR also showing resistance to the third generation EGFR-TKI was reported during the stage of clinical trial of 6 (non-patent document 8). All the third-generation EGFR-TKIs targeting the T790M secondary-resistant mutant EGFR are irreversible inhibitors and show strong antitumor activity based on a covalent bond formation between the side chain thiol group of Cys797 which is present in the EGFR kinase domain and the acrylamide site of the inhibitor. Therefore, the mutation from Cys797 to Ser797 possessing a less reactive side chain hydroxy group is fatal for the irreversible inhibitors. In fact, not only the irreversible inhibitors but also all existing EGFR-TKIs are ineffective for non-small cell lung cancer having C797S tertiary-resistant mutant EGFR (non-patent document 9). In the future, it is clear that non-small cell lung cancer with C797S tertiary-resistant mutant EGFR will become apparent through the clinical use of the third-generation EGFR-TKI, and the development of a fourth-generation EGFR-TKI effective for this mutant is considered an urgent problem (non-patent document 10).

DOCUMENT LIST

Non-Patent Documents non-patent document 1: V. Sharma, et al. Epidermal growth factor receptor mutations in lung cancer, Nature Reviews, 7, 169-181 (2007)
non-patent document 2: D. Li, et al. BIBW2992, an irreversible EGFR/HER2 inhibitor highly effective in preclinical lung cancer models, Oncogene, 27, 4702-4711 (2008)
non-patent document 3: Y. Kim, et al. The EGFR T790 M Mutation in Acquired Resistance to an Irreversible Second-Generation EGFR Inhibitors, Molecular Cancer Therapeutics, 11, 784-791 (2012)
non-patent document 4: W. Zhou, et al. Novel mutant-selective EGFR kinase inhibitors against EGFR T790 M, Nature, 462, 1070-1074 (2009)
non-patent document 5: A. O. Walter, et al. Discovery of a Mutant-Selective Covalent Inhibitor of EGFR that Overcomes T790 M-Mediated Resistance in NSCLC, Cancer Discovery, 1404-1415 (2013)
non-patent document 6: D. A. E. Cross, et al. AZD9291, an Irreversible EGFR TKI, Overcomes T790 M-Mediated Resistance to EGFR Inhibitors in Lung Cancer, Cancer Discovery, 1047-1061 (2014)
non-patent document 7: FDA News Release, FDA approves new pill to treat certain patients with non-small cell lung cancer, Nov. 13, 2015
non-patent document 8: K. S. Thress, et al. Acquired EGFR C797S mutation mediates resistance to AZD9291 in non-small cell lung cancer harboring EGFR T790 M, Nature Medicine, 21, 560-564 (2015)
non-patent document 9: D. Ercan, et al. EGFR Mutations and Resistance to Irreversible Pyrimidine-Based Inhibitors, Clinical Cancer Research, 21, 3913-3923 (2015)
non-patent document 10: Y. Jia, et al. Overcoming EGFR (T790 M) and EGFR(C797S) resistance with mutant-selective allosteric inhibitors, Nature, 534, 129-132 (2016)

SUMMARY OF THE INVENTION

Problems to be Solved by the Invention

An object of the present invention is to provide a fourth-generation EGFR-TKI effective for C797S resistant mutant EGFR (particularly C797S mutant tertiary-resistant EGFR).

Means of Solving the Problems

The present inventors have conducted intensive studies in an attempt to solve the above-mentioned problems and found that a compound represented by the following formula (I) has a specific tyrosine kinase inhibitory activity against C797S resistant mutant EGFR (particularly C797S tertiary-resistant mutant EGFR), which resulted in the completion of the present invention.

Specifically, the present inventors conducted activity evaluation of lamellarins against cancer-related kinases as part of the development and study of an anticancer drug using the marine natural product lamellarin as a structural motif. As a result, it was found that lamellarin N (7) exhibits inhibitory activity against resistant mutant EGFR (L858R/T790M) Lamellarin N (7) is a reversible inhibitor and expression of activity thereof does not depend on the formation of a covalent bond with Cys797. Thus, it was considered a hit compound for creating EGFR-TKI effective for C797S mutation. To improve the activity of the hit compound, docking simulation of lamellarin N (7) with the EGFR (L858R/T790M) kinase domain was executed (FIG. 1). As a result, it was expected that enhanced interaction between the ring A substituent of lamellarin N (7) oriented in the opening of the ATP binding pocket of the kinase and the neighboring Phe795, Asp800 and Glu804 leads to the improvement of the activity. Thus, novel lamellarin N derivatives were synthesized by introducing various substituents into the oxygen functionalities (OH, OMe) of the ring A part of lamellarin N (7) and evaluation of the derivatives were carried out. In addition, similar structural development was also performed for azalamellarin N (8) in which a lactone ring (ring B) of lamellarin N (7) was substituted by a lactam ring.

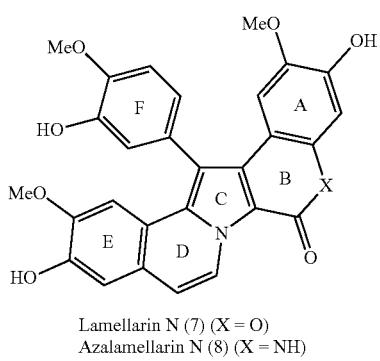

Lamellarin N (7) (X = O)
Azalamellarin N (8) (X = NH)

That is, the present invention provides the following.

[1] A compound represented by the formula (I):

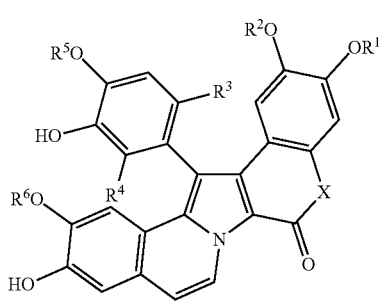

(I)

wherein
X is O or NH,
$R^1$ and $R^2$ are each independently a hydrogen atom or an optionally substituted hydrocarbon group;
$R^3$ and $R^4$ are each independently a hydrogen atom, a halogen atom or an optionally substituted hydrocarbon group, and
$R^5$ and $R^6$ are each independently an optionally substituted hydrocarbon group, excluding the following compounds:

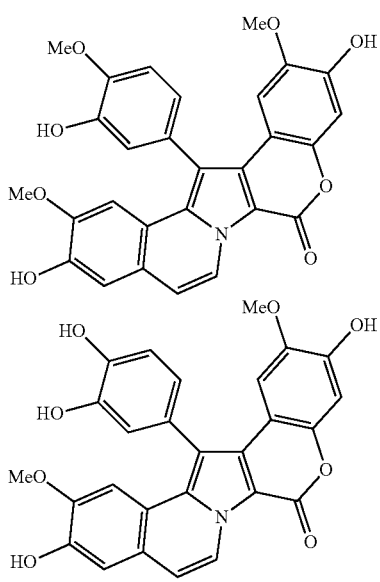

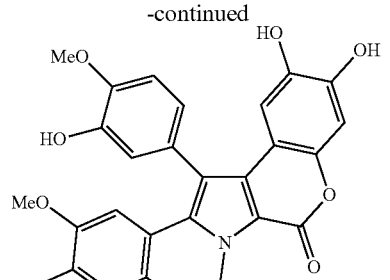

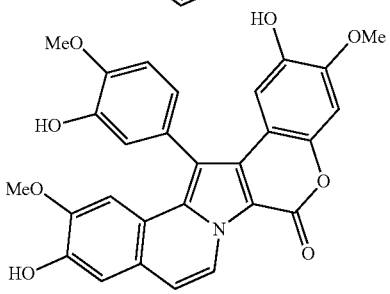

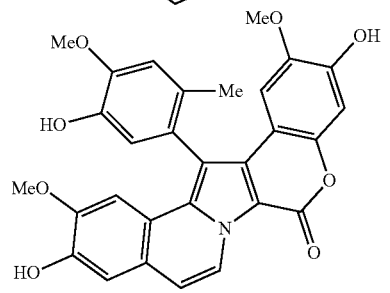

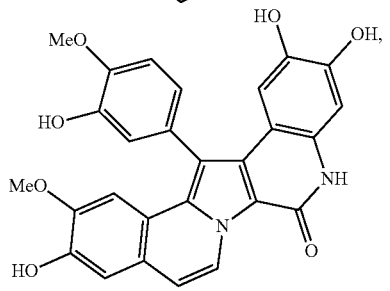

or a salt thereof (sometimes to be abbreviated as "compound (I)" in the present specification).

[2] A C797S mutant resistant EGFR specific tyrosine kinase inhibitor comprising a compound represented by the formula (I):

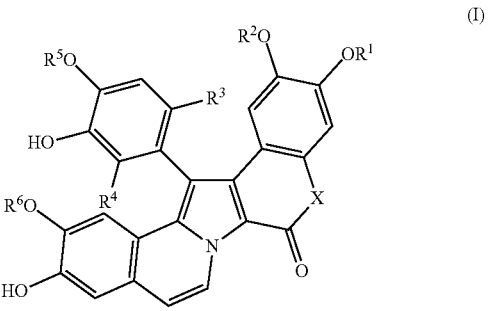

(I)

wherein

X is O or NH, $R^1$ and $R^2$ are each independently a hydrogen atom or an optionally substituted hydrocarbon group;

$R^3$ and $R^4$ are each independently a hydrogen atom, a halogen atom or an optionally substituted hydrocarbon group, and $R^5$ and $R^6$ are each independently an optionally substituted hydrocarbon group, or a salt thereof.

Effect of the Invention

The compound of the present invention has a tyrosine kinase inhibitory activity specific to C797S mutant resistant EGFR (particularly C797S mutant tertiary-resistant EGFR) and is useful as a C797S mutant resistant EGFR (particularly C797S mutant tertiary-resistant EGFR) specific tyrosine kinase inhibitor, an agent for preventing and/or treating non-small cell lung cancer with resistance mutant EGFR and the like, and the like.

DESCRIPTION OF EMBODIMENTS

Figure 1:
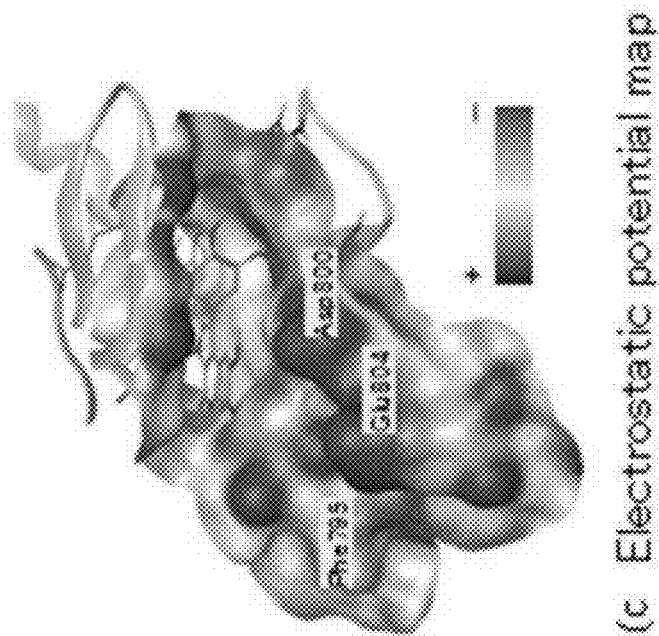
FIG. 1 shows a docking simulation of lamellarin N (7) to the EGFR (L858R/T790M) kinase domain.
Figure 1:
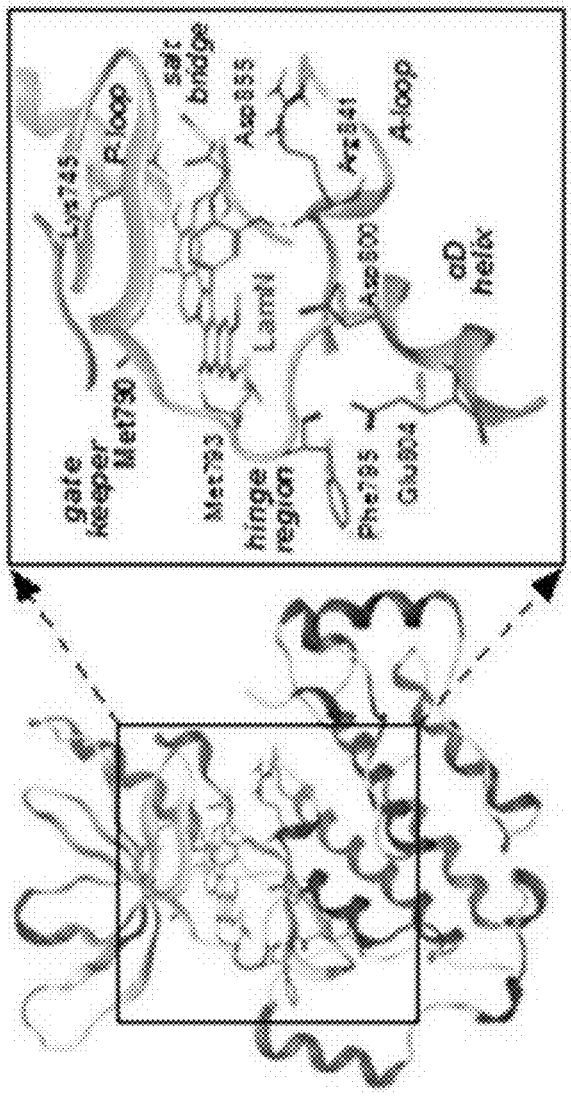

The present invention is explained in detail in the following.

In the following, the definition of each substituent used in the present specification is described. Unless particularly indicated, each substituent has the following definition.

In the present specification, examples of the "halogen atom" include fluorine, chlorine, bromine and iodine.

In the present specification, examples of the "hydrocarbon group" include $C_{1-6}$ alkyl group, $C_{2-6}$ alkenyl group, $C_{2-6}$ alkynyl group, $C_{3-10}$ cycloalkyl group, $C_{3-10}$ cycloalkenyl group, $C_{6-14}$ aryl group and $C_{7-16}$ aralkyl group.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the substituent of the "optionally substituted hydrocarbon group" include halogen atom, hydroxy group, cyano group, nitro group, carboxy group, amino group optionally mono- or di-substituted by $C_{1-6}$ alkyl group and guanidino group. The number of the substituent is, for example, 1-5, preferably 1-3. When plural substituents are present, respective substituents may be the same or different.

The definition of each symbol in the formula (I) is explained below.

X is O or NH.

$R^1$ and $R^2$ are each independently a hydrogen atom or an optionally substituted hydrocarbon group.

As the "hydrocarbon group" of the "optionally substituted hydrocarbon group" for $R^1$ or $R^2$, a $C_{1-6}$ alkyl group (e.g., methyl, ethyl, n-propyl) is preferable.

$R^1$ and $R^2$ are preferably each independently a hydrogen atom or an optionally substituted $C_{1-6}$ alkyl group (e.g., methyl, ethyl, n-propyl), more preferably each independently a hydrogen atom or a $C_{1-6}$ alkyl group (e.g., methyl, ethyl, n-propyl) optionally substituted by 1 to 3 substituents selected from an amino group optionally mono- or di-substituted by a $C_{1-6}$ alkyl group (e.g., dimethylamino) and a guanidino group, further preferably each independently a hydrogen atom, or a $C_{1-6}$ alkyl group (e.g., methyl, ethyl, n-propyl) optionally substituted by an amino group di-substituted by a $C_{1-6}$ alkyl group (e.g., dimethylamino).

$R^3$ and $R^4$ are each independently a hydrogen atom, a halogen atom or an optionally substituted hydrocarbon group.

As the "hydrocarbon group" of the "optionally substituted hydrocarbon group" for $R^3$ or $R^4$, a $C_{1-6}$ alkyl group (e.g., methyl) is preferable.

$R^3$ and $R^4$ are preferably each independently a hydrogen atom, a halogen atom or an optionally substituted $C_{1-6}$ alkyl group (e.g., methyl), more preferably each independently a hydrogen atom or a halogen atom, further preferably each a hydrogen atom.

$R^5$ and $R^6$ are each independently an optionally substituted hydrocarbon group.

As the "hydrocarbon group" of the "optionally substituted hydrocarbon group" for $R^5$ or $R^6$, a $C_{1-6}$ alkyl group (e.g., methyl) is preferable.

$R^5$ and $R^6$ are preferably each independently an optionally substituted $C_{1-6}$ alkyl group (e.g., methyl), more preferably each independently a $C_{1-6}$ alkyl group (e.g., methyl).

As preferable examples of compound (I), the following compounds can be mentioned.

[Compound I-1]

Compound (I) wherein

X is O or NH;

$R^1$ and $R^2$ are each independently a hydrogen atom or an optionally substituted $C_{1-6}$ alkyl group (e.g., methyl, ethyl, n-propyl);

$R^3$ and $R^4$ are each independently a hydrogen atom, a halogen atom or an optionally substituted $C_{1-6}$ alkyl group (e.g., methyl); and $R^5$ and $R^6$ are each independently an optionally substituted $C_{1-6}$ alkyl group (e.g., methyl).

[Compound I-2]

Compound (I) wherein

X is O or NH;

$R^1$ and $R^2$ are each independently a hydrogen atom or a $C_{1-6}$ alkyl group (e.g., methyl, ethyl, n-propyl) optionally substituted by 1 to 3 substituents selected from an amino group optionally mono- or di-substituted by a $C_{1-6}$ alkyl group (e.g., dimethylamino) and a guanidino group;

$R^3$ and $R^4$ are each independently a hydrogen atom, a halogen atom or a $C_{1-6}$ alkyl group (e.g., methyl); and $R^5$ and $R^6$ are each independently a $C_{1-6}$ alkyl group (e.g., methyl).

[Compound I-3]

Compound (I) wherein

X is O or NH;

$R^1$ and $R^2$ are each independently a hydrogen atom or a $C_{1-6}$ alkyl group (e.g., methyl, ethyl, n-propyl) optionally substituted by 1 to 3 substituents selected from an amino group optionally mono- or di-substituted by a $C_{1-6}$ alkyl group (e.g., dimethylamino) and a guanidino group;

$R^3$ and $R^4$ are each independently a hydrogen atom or a halogen atom; and $R^5$ and $R^6$ are each independently a $C_{1-6}$ alkyl group (e.g., methyl).

[Compound I-4]

Compound (I) wherein

X is O or NH;

$R^1$ and $R^2$ are each independently a hydrogen atom or a $C_{1-6}$ alkyl group (e.g., methyl, ethyl, n-propyl) optionally substituted by an amino group di-substituted by a $C_{1-6}$ alkyl group (e.g., dimethylamino);

$R^3$ and $R^4$ are each a hydrogen atom; and $R^5$ and $R^6$ are each independently a $C_{1-6}$ alkyl group (e.g., methyl).

When compound (I) is a salt, examples of such salt include salts with inorganic bases, salts with organic bases, salts with inorganic acids, salts with organic acids, salt with basic or acidic amino acids and the like.

Preferable examples of the salt with inorganic base include alkali metal salts such as sodium salt, potassium salt and the like; alkaline earth metal salts such as calcium salt, magnesium salt and the like; aluminum salt; and ammonium salt.

Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine and N,N-dibenzylethylenediamine.

Preferable examples of the salt with inorganic acid include salts with hydrogen chloride, hydrogen bromide, nitric acid, sulfuric acid and phosphoric acid.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid and p-toluenesulfonic acid.

Preferable examples of the salt with basic amino acid include salts with arginine, lysine and ornithine.

Preferable examples of the salt with acidic amino acid include salts with aspartic acid and glutamic acid.

Among these salts, pharmaceutically acceptable salts are preferable. Examples of the pharmaceutically acceptable salt when the compound has a basic functional group include salts with inorganic acids such as hydrochloric acid, hydrobromic acid, nitric acid, sulfuric acid, phosphoric acid and the like; and salts with organic acids such as acetic acid, phthalic acid, fumaric acid, oxalic acid, tartaric acid, maleic acid, citric acid, succinic acid, methanesulfonic acid, p-toluenesulfonic acid and the like. When the compound has an acidic functional group, inorganic salts such as alkali metal salt (e.g., sodium salt, potassium salt etc.), alkaline earth metal salt (e.g., calcium salt, magnesium salt, barium salt etc.) and the like; ammonium salt and the like can be mentioned.

The compound (I) may be labeled with an isotope (e.g., $^3H$, $^{13}C$, $^{14}C$, $^{18}F$, $^{35}S$, $^{125}I$) or the like.

Furthermore, compound (I) may be a hydrate or a non-hydrate, or a non-solvate or a solvate.

Furthermore, a deuterium conversion form wherein $^1H$ is converted to $^2H(D)$ is also encompassed in compound (I).

When compound (I) has an asymmetric center, isomers such as enantiomer, diastereomer and the like may exist. All such isomers and mixtures thereof are encompassed in the scope of the present invention. In some cases, isomers due to conformation or tautomerism may be produced. Such isomers and mixtures thereof are encompassed in the present invention. Further, when atropisomer is produced (specifically, the formula (I) wherein one or both of $R^3$ and $R^4$ is/are other than a hydrogen atom), such isomers and mixtures thereof are encompassed in compound (I) of the present invention.

The production method of compound (I) of the present invention is explained below.

The compound (I) of the present invention can be synthesized by, for example, the modular synthesis method of lamellarins described in J. Org. Chem. 2014, 79, 529-537 or a method analogous thereto and the like. As one embodiment, the synthesis scheme of compound (I) wherein $R^5$ and $R^6$ are methyl is shown below.

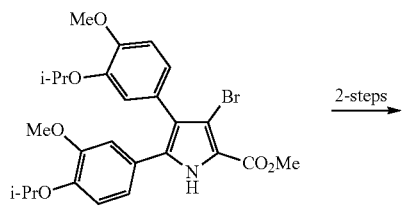

9

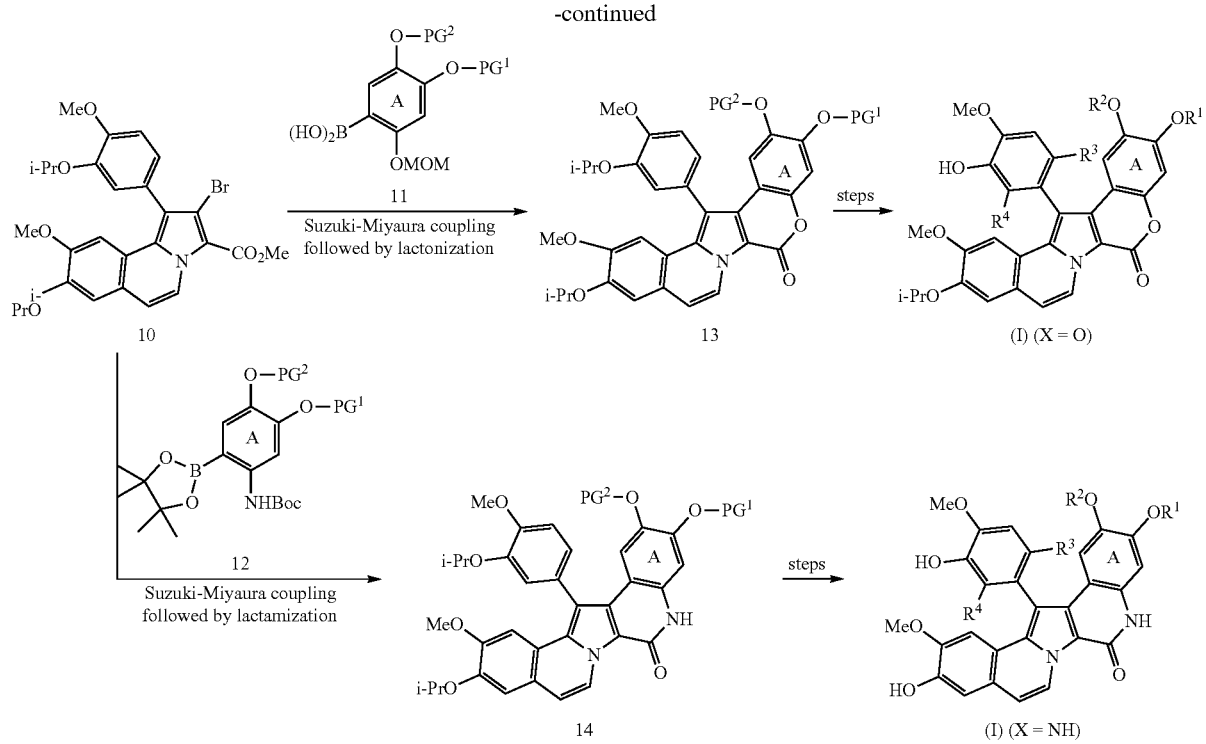

wherein PG[1] and PG[2] are each a protecting group of a hydroxy group, and other symbols are as defined above.

Using compound 9 synthesizable from commercially available pyrrole as a starting material, tricyclic compound 10 can be synthesized in two steps. Lamellarin derivative 13 and azalamellarin derivative 14 can be synthesized by subjecting the compound 10 and arylboronic acid 11 or arylboronate 12 to Suzuki-Miyaura coupling. Further, the protecting groups (PG[1], PG[2]) on oxygen in ring A of lamellarin derivative 13 and azalamellarin derivative 14 are selectively deprotected and the obtained phenol derivatives are further functionalized, whereby compound (I) of the present invention (lamellarin N derivative (X=O) and azalamellarin N derivative (X=NH)) can be synthesized.

The compound (I) of the present invention has a tyrosine kinase inhibitory activity specific to C797S mutant resistant EGFR (particularly C797S tertiary-resistant mutant EGFR) and can be useful as a C797S resistant mutant EGFR (particularly C797S tertiary-resistant mutant EGFR) specific tyrosine kinase inhibitor, an agent for preventing and/or treating non-small cell lung cancer with resistant mutant EGFR and the like, and the like.

The compound (I) of the present invention shows a tyrosine kinase inhibitory activity specific to C797S resistant mutant EGFR (particularly C797S tertiary-resistant mutant EGFR) and is also superior in efficacy expression, pharmacokinetics (e.g., absorbability, distribution, metabolism, excretion), solubility (e.g., water solubility), interaction with other pharmaceutical products (e.g., drug-metabolizing enzyme inhibitory action), safety (e.g., acute toxicity, chronic toxicity, genetic toxicity, reproductive toxicity, cardiotoxicity, carcinogenicity, central toxicity), stability (e.g., chemical stability, stability to enzyme). Thus, compound (I) of the present invention can be useful as a medicament.

Therefore, compound (I) of the present invention can be used for inhibiting a tyrosine kinase action specific to C797S mutant resistant EGFR (particularly C797S tertiary-resistant mutant EGFR) in mammals (e.g., mouse, rat, hamster, rabbit, cat, dog, bovine, sheep, monkey, human).

The compound (I) of the present invention may be administered as a medicine orally or parenterally to a mammal (preferably human) as it is or in combination with a pharmacologically acceptable carrier.

A medicament containing compound (I) of the present invention (sometimes to be abbreviated as "the medicament of the present invention") is described in detail below. Examples of the dosage form of the medicament of the present invention include oral agents such as tablet (e.g., sugar-coated tablet, film-coated tablet, sublingual tablet, buccal tablet, intraorally quick-integrating tablet), pill, granule, powder, capsule (e.g., soft capsule, microcapsule), syrup, emulsion, suspension, film (e.g., intraorally disintegrating film, oral mucosa adhesive film) and the like. Examples of the dosage form of the medicament of the present invention also include parenteral agents such as injection, drip transfusion, transdermal agent (e.g., iontophoresis transdermal agent), suppository, ointment, nasal preparation, pulmonary preparation, eye drop and the like. The medicament of the present invention may also be a controlled-release preparation such as an immediate-release preparation, a sustained-release preparation (e.g., sustained-release microcapsule) and the like.

The medicament of the present invention may be produced by a known production method (e.g., method described in the Japanese Pharmacopoeia) generally used in the technical field of preparation formulation. In addition, the medicament of the present invention can appropriately contain, where necessary, appropriate amounts of additives generally used in the pharmaceutical field such as excipient, binder, disintegrant, lubricant, sweetening agent, surfactant, suspending agent, emulsifier, colorant, preservative, aromatic, corrigent, stabilizer, thickening agent and the like.

As the aforementioned pharmacologically acceptable carrier, these additives can be mentioned.

For example, tablet can be produced using excipient, binder, disintegrant, lubricant and the like, and pill and granule can be produced using excipient, binder and disintegrant. Powder and capsule can be produced using excipient and the like, syrup can be produced using sweetening agent and the like, and emulsion and suspension can be produced using suspending agent, surfactant, emulsifier and the like.

Examples of the excipient include lactose, sucrose, glucose, starch, saccharose, microcrystalline cellulose, *Glycyrrhiza uralensis*, mannitol, sodium hydrogen carbonate, calcium phosphate and calcium sulfate.

Examples of the binder include 5 to 10 wt % starch paste solution, 10 to 20 wt % gum arabic solution or gelatin solution, 1 to 5 wt % tragacanth solution, carboxymethylcellulose solution, sodium alginate solution and glycerol.

Examples of the disintegrant include starch and calcium carbonate.

Examples of the lubricant include magnesium stearate, stearic acid, calcium stearate and purified talc.

Examples of the sweetening agent include glucose, fructose, invert sugar, sorbitol, xylitol, glycerol and simple syrup.

Examples of the surfactant include sodium lauryl sulfate, polysorbate 80, sorbitan monofatty acid ester and polyoxyl 40 stearate.

Examples of the suspending agent include gum arabic, sodium alginate, sodium carboxymethylcellulose, methylcellulose and bentonite.

Examples of the emulsifier include gum arabic, tragacanth, gelatin and polysorbate 80.

For example, when the medicament of the present invention is a tablet, the tablet can be produced according to a method known per se by adding, for example, excipient (e.g., lactose, sucrose, starch), disintegrant (e.g., starch, calcium carbonate), binder (e.g., starch, gum arabic, carboxymethylcellulose, polyvinylpyrrolidone, hydroxypropylcellulose) or lubricant (e.g., talc, magnesium stearate, polyethylene glycol 6000) to compound (I) of the present invention, compression molding the mixture and, where necessary, coating same by a method known per se for masking of taste, or enteric or sustainability purpose. As the coating agent used for coating, hydroxypropylmethylcellulose, ethylcellulose, hydroxymethylcellulose, hydroxypropylcellulose, polyoxyethylene glycol, Tween 80, pluronic F68, cellulose acetate phthalate, hydroxypropylmethylcellulose phthalate, hydroxymethylcellulose acetate succinate, Eudragit (manufactured by Rohm, Germany, methacrylic acid-acrylic acid copolymer) or dye (e.g., red iron oxide, titanium dioxide) can be used.

The aforementioned injection includes intravenous injection, subcutaneous injection, intradermal injection, intramuscular injection, intraperitoneal injection, drip injection and the like.

Such injection is prepared by a method known per se, namely, by dissolving, suspending or emulsifying compound (I) of the present invention in an aseptic aqueous solution or an oily liquid. Examples of the aqueous solution include an isotonic solution (e.g., D-sorbitol, D-mannitol, sodium chloride) containing physiological saline, glucose or other auxiliary agent and the like. The aqueous solution may contain a suitable solubilizing agent, for example, alcohol (e.g., ethanol), polyalcohol (e.g., propylene glycol, polyethylene glycol), non-ionic surfactant (e.g., polysorbate 80, HCO-50). As the oily liquid, sesame oil, soybean oil and the like can be mentioned. The oily liquid may contain a suitable solubilizing agent. As the solubilizing agent, benzyl benzoate, benzyl alcohol and the like can be mentioned. The injection may contain a buffering agent (e.g., phosphate buffer, sodium acetate buffer), a soothing agent (e.g., benzalkonium chloride, procaine hydrochloride), a stabilizer (e.g., human serum albumin, polyethylene glycol), a preservative (e.g., benzyl alcohol, phenol) or the like. The prepared injection can be generally filled in an ampoule.

The content of compound (I) of the present invention in the medicament of the present invention is varies depending on the form of the preparation. It is generally about 0.01 to about 100 wt %, preferably about 2 to about 85 wt %, further preferably about 5 to about 70 wt %, relative to the whole preparation.

The content of the additive in the medicament of the present invention varies depending on the form of the preparation. It is generally about 1 to about 99.9 wt %, preferably about 10 to about 90 wt %, relative to the whole preparation.

The compound (I) of the present invention is stable and low toxic and can be used safely. The daily dose of compound (I) of the present invention varies depending on the condition and body weight of patients, the kind of compound, administration route and the like. For example, for oral administration to patients for the treatment of cancer, the dose per day for an adult (body weight about 60 kg) is about 1 to about 1000 mg, preferably about 3 to about 300 mg, further preferably about 10 to about 200 mg, of compound (I) of the present invention, which may be administered in one to three portions.

When compound (I) of the present invention is parenterally administered, it is generally administered in the form of a liquid (e.g., injection). A single dose of compound (I) of the present invention varies depending on the subject of administration, target organ, symptom, administration method and the like. For example, it is generally preferable to administer about 0.01 to about 100 mg, preferably about 0.01 to about 50 mg, more preferably about 0.01 to about 20 mg, of compound (I) of the present invention per 1 kg body weight by intravenous injection.

EXAMPLES

While the present invention is more specifically explained in the following by referring to Examples, the present invention is not limited by the following Examples. It is needless to say that the present invention can be carried out with appropriate modification within a range that can meet the above-mentioned and the below-mentioned gist, and they are encompassed in the technical scope of the present invention.

In the present specification, the abbreviations used in the following schemes mean the following.

Me: methyl group
Et: ethyl group
OMe: methoxy group
Oi-Pr: isopropoxy group
$CO_2Me$: methoxycarbonyl group
$NMe_2$: dimethylamino group
MOM: methoxymethyl group
OMOM: methoxymethoxy group
OBn: benzyloxy group
Boc: tert-butoxycarbonyl group
NHBoc: tert-butoxycarbonylamino group

[Synthesis Method of Lamellarin N Derivatives]

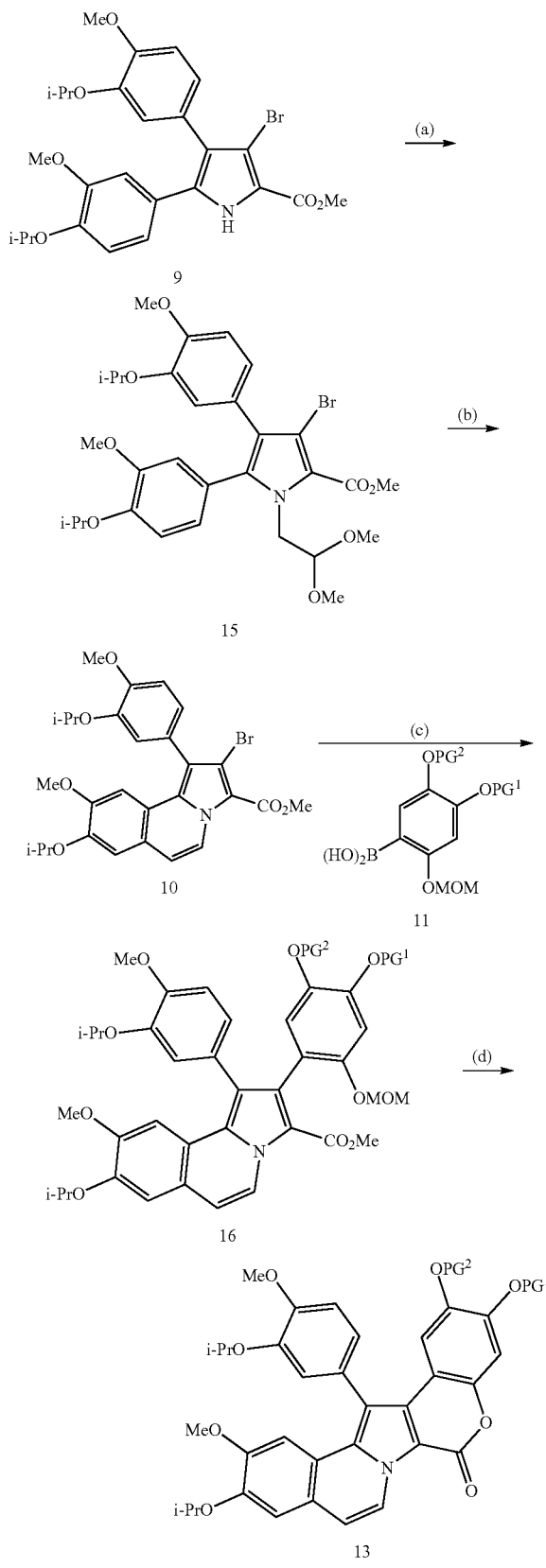

Compound 9 can be synthesized by the method described in J. Org. Chem. 2014, 79, 529-537 or a method analogous thereto.

Step (a): Synthesis of Compound 15

Under an argon atmosphere, a mixture of compound 9 (2.66 g, 5.00 mmol), 2-bromo-1,1-dimethoxyethane (3.72 mL, 31.5 mmol), cesium carbonate (11.7 g, 35.8 mmol), and dry dimethylformamide (60 mL) was stirred at 110° C. for 16 hr. After allowing to cool, water was added and the mixture was extracted with a hexane/ethyl acetate mixed solvent (1:1). The extract was washed successively with water and saturated brine, and dried over anhydrous sodium sulfate, and the solvent was evaporated under reduced pressure. The residue was purified by silica gel flash chromatography (hexane:ethyl acetate=3:1) to give compound 15 as a white semisolid (2.83 g). yield 91%.

$^1$H NMR (400 MHz, CDCl$_3$): δ 1.21 (d, J=6.1 Hz, 6H), 1.35 (d, J=6.1 Hz, 6H), 3.23 (s, 6H), 3.67 (s, 3H), 3.81 (s, 3H), 3.93 (s, 3H), 4.27 (sep, J=6.1 Hz, 1H), 4.41-4.46 (m, 3H), 4.50 (sep, J=6.1 Hz, 1H), 6.66 (s, 1H), 6.72-6.76 (m, 3H), 6.76 (d, J=1.7 Hz, 1H), 6.79 (d, J=8.3 Hz, 1H).

HRDARTMS m/z. Calcd for C$_{30}$H$_{38}$BrNO$_8$(M$^+$): 619.1781. Found: 619.1782.

Step (b): Synthesis of Compound 10

Under an argon atmosphere, to a solution of compound 15 (1.84 g, 2.97 mmol) in dichloromethane (110 mL) was added trimethylsilyl trifluoromethanesulfonate (270 μL, 1.49 mmol) at 0° C. After stirring at 0° C. for 1.5 hr, a saturated aqueous sodium hydrogen carbonate solution was added, and the mixture was warmed to room temperature and stirred at the same temperature for 30 min. Water was added and the mixture was extracted with dichloromethane. The extract was washed successively with water and saturated brine and dried over anhydrous sodium sulfate, and dichloromethane was evaporated under reduced pressure. The residue was purified by silica gel flash chromatography (hexane:ethyl acetate=4:1) to give compound 10 as a white solid (1.50 g). yield 91%. melting point 165-166° C. (diethyl ether/hexane mixed solvent).

$^1$H NMR (400 MHz, CDCl$_3$): δ 1.35 (d, J=6.1 Hz, 3H), 1.38 (d, J=6.1 Hz, 3H), 1.42 (d, J=6.1 Hz, 6H), 3.41 (s, 3H), 3.93 (s, 3H), 3.98 (s, 3H), 4.53 (sep, J=6.1 Hz, 1H), 4.66 (sep, J=6.1 Hz, 1H), 6.93 (d, J=7.6 Hz, 1H), 6.95 (d, J=1.9 Hz, 1H), 6.99 (dd, J=1.9 and 8.2 Hz, 1H), 7.02 (s, 1H), 7.05 (d, J=8.2 Hz, 1H), 7.07 (s, 1H), 9.28 (d, J=7.6 Hz, 1H).

HRDARTMS m/z. Calcd for C$_{28}$H$_{31}$BrNO$_6$[(M+H)$^+$]: 556.13347. Found: 556.13474.

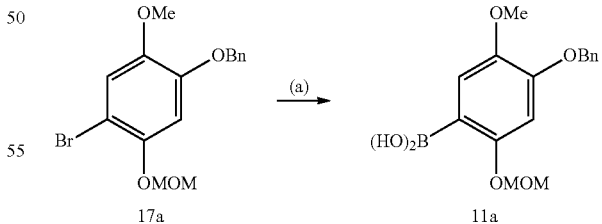

Step (a): Synthesis of Compound 11a

Under an argon atmosphere, to a solution of compound 17a (13.8 g, 39.1 mmol), which was commercially available or synthesized by a method known per se or a method analogous thereto, in tetrahydrofuran (120 mL) was added dropwise a pentane solution of tert-butyllithium (1.35 M, 60.9 mL, 82.2 mmol) at −78° C. and the mixture was stirred at the same temperature for 1 hr. Trimethyl borate (6.54 mL, 58.7 mmol) was added dropwise at −78° C., and the mixture was stirred at the same temperature for 1 hr, and the mixture was allowed to warm to room temperature and stirred at the same temperature for 1 hr. Saturated aqueous ammonium chloride solution was added to the reaction solution, and the solvent was evaporated under reduced pressure. Acetic acid was added by small portions to the residue to adjust to pH=3. Thereafter, the mixture was extracted with dichloromethane and the extract was washed successively with water, saturated aqueous sodium hydrogen carbonate solution, and saturated brine, and dried over anhydrous sodium sulfate. Dichloromethane was evaporated under reduced pressure and the residue was washed with hexane to give compound 11a as a pale-yellow solid (12.3 g). yield 99%.

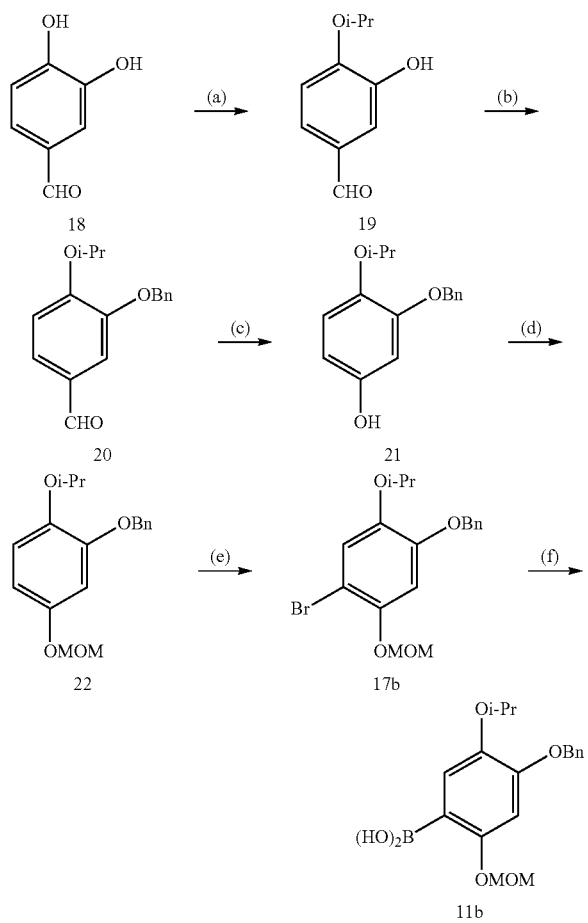

Step (a): Synthesis of Compound 19

Under an argon atmosphere, to a solution of compound 18 (5.01 g, 36.2 mmol), which was commercially available or synthesized by a method known per se or a method analogous thereto, in dry dimethylformamide (30 mL) were successively added potassium carbonate (5.00 g, 36.2 mmol), potassium iodide (6.02 g, 36.3 mmol), and 2-bromopropane (4.42 mL, 47.1 mmol). The mixture was stirred at 40° C. for 21 hr. After allowing to cool, 2 M hydrochloric acid was added, and the mixture was extracted with ethyl acetate. The extract was washed successively with water and saturated brine and dried over anhydrous sodium sulfate, and ethyl acetate was evaporated under reduced pressure. The residue was purified by silica gel column chromatography (hexane:ethyl acetate=5:1-1:1) to give compound 19 as a white solid (4.25 g). yield 65%.

$^1$H NMR (400 MHz, CDCl$_3$): δ 1.42 (d, J=6.1 Hz, 6H), 4.74 (sep, J=6.1 Hz, 1H), 5.94 (br s, 1H), 6.96 (d, J=8.2 Hz, 1H), 7.41 (dd, J=2.0 and 8.0 Hz, 1H), 7.45 (d, J=2.0 Hz, 1H), 9.83 (s, 1H).

Step (b): Synthesis of Compound 20

Under an argon atmosphere, to a solution of compound 19 (3.89 g, 21.6 mmol) in dry acetone (40 mL) were successively added potassium carbonate (3.87 g, 36.2 mmol) and benzyl bromide (3.33 mL, 28.0 mmol). The mixture was heated under reflux for 21 hr. After allowing to cool, 2 M hydrochloric acid was added, and the solvent was evaporated under reduced pressure. Water was added to the residue, and the mixture was extracted with ethyl acetate. The extract was washed successively with water and saturated brine and dried over anhydrous sodium sulfate, and ethyl acetate was evaporated under reduced pressure. The residue was purified by silica gel column chromatography (hexane:ethyl acetate=5:1) to give compound 20 as a white solid (5.71 g). yield 98%.

$^1$H NMR (400 MHz, CDCl$_3$): δ 1.41 (d, J=6.0 Hz, 6H), 4.68 (sep, J=6.0 Hz, 1H), 5.17 (s, 2H), 7.00 (d, J=8.2 Hz, 1H), 7.29-7.47 (m, 7H), 9.80 (s, 1H).

Step (c): Synthesis of Compound 21

Under an argon atmosphere, to a solution of compound 20 (1.02 g, 3.79 mmol) in dichloromethane (12 mL) was added m-chloroperbenzoic acid (containing about 30% water, 1.31 g) at 0° C. After stirring at 0° C. for 18 hr, a saturated aqueous sodium hydrogen carbonate solution was added, and the mixture was allowed to warm to room temperature and extracted with dichloromethane. The extract was washed with water and dried over anhydrous sodium sulfate, and ethyl acetate was evaporated under reduced pressure. Under an argon atmosphere, a mixture of the residue, potassium carbonate (1.27 g, 4.28 mmol), and methanol (13 mL) was stirred at room temperature for 30 min. Methanol was evaporated under reduced pressure. Water was added to the residue and the mixture was extracted with dichloromethane. The extract was washed successively with water and saturated brine and dried over anhydrous sodium sulfate, and dichloromethane was evaporated under reduced pressure. The residue was purified by silica gel column chromatography (hexane:ethyl acetate=3:1-1:1-ethyl acetate) to give compound 21 as a yellow oil (785 mg). yield 80%.

$^1$H NMR (400 MHz, CDCl$_3$): δ 1.29 (d, J=6.0 Hz, 6H), 4.34 (sep, J=6.0 Hz, 1H), 5.01 (s, 2H), 5.13 (br s, 1H), 6.31 (dd, J=2.8 and 8.6 Hz, 1H), 6.45 (d, J=2.8 Hz, 1H), 6.80 (d, J=8.6 Hz, 1H), 7.27-7.41 (m, 5H).

Step (d): Synthesis of Compound 22

Under an argon atmosphere, to a solution of compound 21 (785 mg, 3.04 mmol) and N,N-diisopropylethylamine (1.06 mL, 6.08 mmol) in dichloromethane (11.5 mL) was added chlorodimethyl ether (0.35 mL, 4.56 mmol) at 0° C. and the mixture was stirred at the same temperature for 1 hr. After allowing to warm to room temperature, the mixture was stirred at the same temperature for 18 hr. 28% Aqueous ammonia was added and the mixture was extracted with dichloromethane. The extract was washed successively with water and saturated brine and dried over anhydrous sodium sulfate, and dichloromethane was evaporated under reduced pressure. The residue was purified by silica gel column chromatography (hexane:ethyl acetate=5:1-1:1-ethyl acetate) to give compound 22 as a pale-yellow oil (856 mg). yield 93%.

$^1$H NMR (400 MHz, CDCl$_3$): δ 1.31 (d, J=6.2 Hz, 6H), 3.45 (s, 3H), 4.38 (sep, J=6.1 Hz, 1H), 5.08 (s, 2H), 5.09 (s, 2H), 6.57 (dd, J=2.9, 8.7 Hz, 1H), 6.68 (d, J=2.8 Hz, 1H), 6.86 (d, J=8.7 Hz, 1H), 7.28-7.45 (m, 5H).

Step (e): Synthesis of Compound 17b

Under an argon atmosphere, to a solution of compound 22 (201 mg, 0.663 mmol) in dry dimethylformamide (3.3 mL) was added N-bromosuccinimide (119 mg, 0.668 mmol) at 0° C. After stirring at 0° C. for 2 hr, water was added and the mixture was extracted with dichloromethane. The extract was washed successively with water and saturated brine and dried over anhydrous sodium sulfate, and dichloromethane was evaporated under reduced pressure. The residue was purified by silica gel column chromatography (hexane:ethyl acetate=10:1) to give compound 17b as a pale-yellow oil (232 mg). yield 92%.

$^1$H NMR (400 MHz, CDCl$_3$): δ 1.32 (d, J=6.1 Hz, 6H), 3.48 (s, 3H), 4.40 (sep, J=6.1 Hz, 1H), 5.09 (s, 2H), 5.10 (s, 2H), 6.83 (s, 1H), 7.10 (s, 1H), 7.28-7.43 (m, 5H).

Step (f): Synthesis of Compound 11b

Under an argon atmosphere, to a solution of compound 17b (574 mg, 1.51 mmol) in tetrahydrofuran (9.5 mL) was added dropwise a hexane solution of n-butyllithium (1.50 M, 1.1 mL, 1.66 mmol) at −100° C., and the mixture was stirred at the same temperature for 20 min. Trimethyl borate (0.30 mL, 2.67 mmol) was added dropwise at −100° C., and the mixture was allowed to warm to room temperature and stirred at the same temperature for 1 hr. Saturated aqueous ammonium chloride solution was added to the reaction solution, and the solvent was evaporated under reduced pressure. Acetic acid was added by small portions to the residue to adjust to pH=3. Thereafter, the mixture was extracted with dichloromethane and the extract was washed successively with water and saturated brine and dried over anhydrous sodium sulfate. Dichloromethane was evaporated under reduced pressure, and the residue was washed with hexane to give compound 11b as a white solid (379 mg). yield 73%.

$^1$H NMR (400 MHz, CDCl$_3$): δ 1.32 (d, J=6.2 Hz, 6H), 3.46 (s, 3H), 4.45 (sep, 1H, 6.1 Hz), 5.15 (s, 2H), 5.16 (s, 2H), 6.32 (br s, 2H), 6.81 (s, 1H), 7.40 (s, 1H), 7.29-7.45 (m, 5H).

Step (a): Synthesis of Compound 17c

Under an argon atmosphere, to a solution of compound 23 (1.20 mg, 3.43 mmol) in dry dimethylformamide (20 mL) was added N-bromosuccinimide (0.64 g, 3.60 mmol) at 0° C. After stirring at 0° C. for 2 hr, water was added and the mixture was extracted with dichloromethane. The extract was washed successively with water and saturated brine and dried over anhydrous sodium sulfate, and dichloromethane was evaporated under reduced pressure. The residue was purified by silica gel column chromatography (hexane:ethyl acetate=7:1) to give compound 17c as a white solid (1.23 g). yield 83%.

Step (b): Synthesis of Compound 11c

Under an argon atmosphere, to a solution of compound 17c (1.22 g, 2.87 mmol) in tetrahydrofuran (50 mL) was added dropwise a solution of n-butyllithium (1.54 M, 2.05 mL, 3.16 mmol) at −78° C. and the mixture was stirred at the same temperature for 1 hr. Trimethyl borate (0.48 mL, 4.31 mmol) was added dropwise at −78° C., and the mixture was allowed to warm to room temperature and stirred at the same temperature for 1 hr. Saturated aqueous ammonium chloride solution was added to the reaction solution, and the solvent was evaporated under reduced pressure. Acetic acid was added by small portions to the residue to adjust to pH=3. Thereafter, the mixture was extracted with dichloromethane and the extract was washed successively with water and saturated brine and dried over anhydrous sodium sulfate. Dichloromethane was evaporated under reduced pressure, and the residue was washed with hexane to give compound 11c as a pale-yellow solid (905 mg). yield 89%.

$^1$H NMR (500 MHz, CDCl$_3$): δ 3.46 (s, 3H), 5.12 (s, 2H), 5.16 (s, 2H), 5.18 (s, 2H), 5.93 (s, 2H), 6.83 (s, 1H), 7.25-7.37 (s, 6H), 7.42-7.46 (m, 5H).

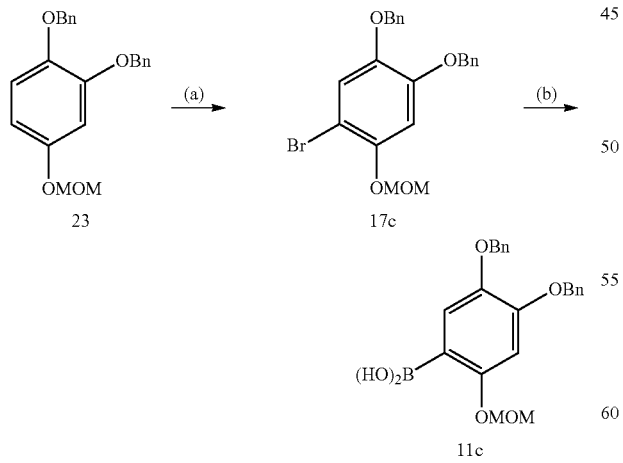

Step (a): Synthesis of Compound 16a

Under an argon atmosphere, a mixture of compound 10 (290 mg, 0.521 mmol), compound 11a (497 mg, 1.56 mmol), bis(dibenzylideneacetone)palladium(0) (30.0 mg, 52.1 μmol), 1,1'-bis(diphenylphosphino)ferrocene (28.9 mg, 52.1 μmol), Na$_2$CO$_3$ (365 mg, 3.44 mmol), 1,2-dimethoxyethane (12 mL), and degassed water (1.0 mL) was heated under reflux for 24 hr. After allowing to cool, the solvent was evaporated under reduced pressure. Water was added to the residue and the mixture was extracted with dichloromethane. The extract was washed successively with water and saturated brine and dried over anhydrous sodium sulfate, and dichloromethane was evaporated under reduced pressure. The residue was purified by silica gel flash chromatography (hexane:ethyl acetate=3:1) to give compound 16a as a pale-brown solid (302 mg). yield 77%.

$^1$H NMR (400 MHz, CDCl$_3$): δ 0.98-1.33 (m, 6H), 1.40-1.48 (m, 6H), 3.22 (br s, 3H), 3.43 (br s, 3H), 3.61 (br s, 6H), 3.84 (br s, 3H), 4.20-4.43 (m, 1H), 4.63-4.95 (m, 3H), 5.06-5.16 (m, 2H), 6.48-7.50 (m, 13H), 9.27 (d, J=7.5 Hz, 1H).

HRDARTMS m/z. Calcd for C$_{44}$H$_{48}$NO$_{10}$[(M+H)$^+$]: 750.32782. Found: 750.32788.

Step (a): Synthesis of Compound 16b

Under an argon atmosphere, a mixture of compound 10 (186 mg, 0.334 mmol), compound 11b (173 mg, 0.500 mmol), bis(dibenzylideneacetone)palladium(0) (19.6 mg, 34.1 μmol), 1,1'-bis(diphenylphosphino)ferrocene (18.3 mg, 33.0 μmol), Na$_2$CO$_3$ (233 mg, 2.20 mmol), 1,2-dimethoxyethane (15 mL) and degassed water (1 mL) was heated under reflux for 24 hr. After allowing to cool, the solvent was evaporated under reduced pressure. Water was added to the residue and the mixture was extracted with dichloromethane. The extract was washed successively with water and saturated brine and dried over anhydrous sodium sulfate, and dichloromethane was evaporated under reduced pressure. The residue was purified by silica gel flash chromatography (hexane:ethyl acetate=2:1) to give compound 16b as a pale-brown solid (55.3 mg). yield 94%.

$^1$H NMR (500 MHz, CDCl$_3$): δ 1.02-1.31 (m, 12H), 1.42 (d, J=6.1 Hz, 6H), 3.23 (br s, 3H), 3.42 (s, 3H), 3.60 (s, 3H), 3.82 (s, 3H), 4.14-4.42 (m, 2H), 4.66 (sep, J=6.1 Hz, 1H), 4.69-4.93 (m, 2H), 5.02-5.13 (m, 2H), 6.57 (br s, 0.5H), 6.66 (br s, 0.5H), 6.75-6.90 (m, 3.5H), 6.91 (d, J=7.6 Hz, 1H), 6.96-7.02 (m, 0.5H), 7.04 (s, 1H), 7.20-7.33 (m, 2H), 7.34-7.39 (m, 2H), 7.42-7.47 (m, 2H), 9.28 (d, J=7.6 Hz, 1H).

HRDARTMS m/z. Calcd for C$_{46}$H$_{52}$NO$_{10}$[(M+H)$^+$]: 778.35912. Found: 778.35688.

Step (a): Synthesis of Compound 16c

Under an argon atmosphere, a mixture of compound 10 (1.23 g, 2.21 mmol), compound 11c (1.31 mg, 3.32 mmol), bis(dibenzylideneacetone)palladium(0) (123 mg, 0.213 mmol), 1,1'-bis(diphenylphosphino)ferrocene (132 mg, 0.237 mmol), Na$_2$CO$_3$ (1.55 g, 14.6 mmol), 1,2-dimethoxyethane (80 mL), and degassed water (6 mL) was heated under reflux for 24 hr. After allowing to cool, the solvent was evaporated under reduced pressure. Water was added to the residue and the mixture was extracted with dichloromethane. The extract was washed successively with water and saturated brine and dried over anhydrous sodium sulfate, and dichloromethane was evaporated under reduced pressure. The residue was purified by silica gel flash chromatography (hexane:ethyl acetate=5:1) to give compound 16c as a pale-yellow solid (1.83 g). yield 100%.

$^1$H NMR (500 MHz, CDCl$_3$): δ 1.03-1.30 (m, 6H), 1.42 (d, J=6.1 Hz, 6H), 3.23 (br s, 3H), 3.42 (s, 3H), 3.56 (br s, 3H), 3.82 (s, 3H), 4.23-4.40 (m, 1H), 4.66 (sep, J=6.1 Hz, 1H), 4.79-4.93 (m, 4H), 5.04-5.14 (m, 2H), 6.63 (br s, 0.5H), 6.71-6.90 (m, 4.5H), 6.91 (d, J=7.6 Hz, 1H), 7.03 (s, 1H), 7.20-7.38 (m, 9H), 7.40-7.45 (m, 2H), 9.27 (d, J=7.6 Hz, 1H).

HRDARTMS m/z. Calcd for C$_{50}$H$_{52}$NO$_{10}$[(M+H)$^+$]: 826.35912. Found: 826.36040.

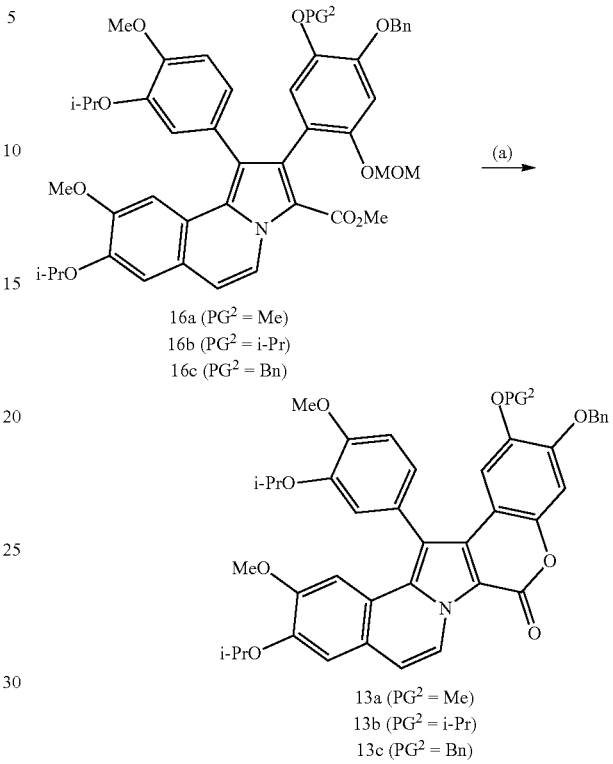

16a (PG$^2$ = Me)
16b (PG$^2$ = i-Pr)
16c (PG$^2$ = Bn)

(a) →

13a (PG$^2$ = Me)
13b (PG$^2$ = i-Pr)
13c (PG$^2$ = Bn)

Step (a): Synthesis of Compound 13a

Under an argon atmosphere, a mixture of compound 16a (30.0 mg, 40.0 μmol), p-toluenesulfonic acid monohydrate (30.4 mg, 0.160 mmol), and methanol (1.5 mL) was stirred in a sealed tube with heating at 65° C. for 18 hr. After allowing to cool, the solvent was evaporated under reduced pressure. Water was added to the residue and the mixture was extracted with dichloromethane. The extract was washed successively with water and saturated brine and dried over anhydrous sodium sulfate, and dichloromethane was evaporated under reduced pressure. The residue was purified by silica gel column chromatography (hexane:ethyl acetate=2:1) to give compound 13a as a pale-yellow solid (25.0 mg). yield 93%.

$^1$H NMR (400 MHz, CDCl$_3$): δ 1.35 (d, J=6.1 Hz, 3H), 1.37 (d, J=6.1 Hz, 3H), 1.43 (d, J=6.1 Hz, 6H), 3.45 (s, 3H), 3.49 (s, 3H), 3.96 (s, 3H), 4.55 (sep, J=6.1 Hz, 1H), 4.69 (sep, J=6.1 Hz, 1H), 5.17 (s, 2H), 6.76 (s, 1H), 6.93 (s, 1H), 7.01 (d, J=7.4 Hz, 1H), 7.09 (s, 1H), 7.14 (d, J=1.8 Hz, 1H), 7.15 (d, J=8.2 Hz, 1H), 7.17 (s, 1H), 7.20 (dd, J=1.8 and 8.2 Hz, 1H), 7.27-7.33 (m, 1H), 7.33-7.40 (m, 2H), 7.40-7.45 (m, 2H), 9.19 (d, J=7.4 Hz, 1H).

HRDARTMS m/z. Calcd for C$_{41}$H$_{40}$NO$_8$[(M+H)$^+$]: 674.27539. Found: 674.27820.

Step (a): Synthesis of Compound 13b

Under an argon atmosphere, a mixture of compound 16b (202 mg, 0.260 mmol), p-toluenesulfonic acid monohydrate (198 mg, 1.04 mmol), and methanol (10 mL) was heated under reflux for 18 hr. After allowing to cool, the solvent was evaporated under reduced pressure. Water was added to the residue and the mixture was extracted with dichloromethane. The extract was washed successively with water and saturated brine and dried over anhydrous sodium sulfate, and dichloromethane was evaporated under reduced pressure. The residue was purified by silica gel column chromatography (hexane:ethyl acetate=2:1) to give compound 13b as a pale-yellow solid (161 mg). yield 88%.

$^1$H NMR (400 MHz, CDCl$_3$): δ 1.19 (d, J=6.1 Hz, 3H), 1.20 (d, J=6.1 Hz, 3H), 1.35 (d, J=6.1 Hz, 3H), 1.36 (d, J=6.1 Hz, 3H), 1.43 (d, J=6.1 Hz, 6H), 3.44 (s, 3H), 3.98 (s, 3H), 4.02 (sep, J=6.1 Hz, 1H), 4.54 (sep, J=6.1 Hz, 1H), 4.69 (sep, J=6.1 Hz, 1H), 5.15 (s, 2H), 6.77 (s, 1H), 6.94 (s, 1H), 7.00 (d, J=7.4 Hz, 1H), 7.08 (s, 1H), 7.11-7.16 (m, 3H), 7.17 (s, 1H), 7.27-7.33 (m, 1H), 7.33-7.39 (m, 2H), 7.40-7.45 (m, 2H), 9.18 (d, J=7.4 Hz, 1H).

HRDARTMS m/z. Calcd for C$_{43}$H$_{44}$NO$_8$[(M+H)$^+$]: 702.30669. Found: 702.30518.

Step (a): Synthesis of Compound 13c

Under an argon atmosphere, a mixture of compound 16c (1.77 g, 2.14 mmol), p-toluenesulfonic acid monohydrate (1.63 g, 8.57 mmol), and methanol (60 mL) was heated under reflux for 18 hr. After allowing to cool, the solvent was evaporated under reduced pressure. Water was added to the residue and the mixture was extracted with dichloromethane. The extract was washed successively with water and saturated brine and dried over anhydrous sodium sulfate, and dichloromethane was evaporated under reduced pressure. The residue was recrystallized from dichloromethane-hexane to give compound 13c as a white solid (1.35 g). yield 84%.

$^1$H NMR (400 MHz, CDCl$_3$): δ 1.34 (d, J=6.1 Hz, 3H), 1.37 (d, J=6.1 Hz, 3H), 1.43 (d, J=6.1 Hz, 3H), 1.43 (d, J=6.1 Hz, 3H), 3.44 (s, 3H), 3.97 (s, 3H), 4.54 (sep, J=6.1 Hz, 1H), 4.69 (sep, J=6.1 Hz, 1H), 4.76 (d, J=12.4 Hz, 1H), 4.78 (d, J=12.4 Hz, 1H), 5.19 (s, 2H), 6.91 (s, 1H), 6.98 (s, 1H), 7.00 (d, J=7.4 Hz, 1H), 7.08 (s, 1H), 7.10 (s, 1H), 7.12 (s, 1H), 7.13-7.16 (m, 2H), 7.23-7.39 (m, 8H), 7.43-7.46 (m, 2H), 9.20 (d, J=7.4 Hz, 1H).

HRDARTMS m/z. Calcd for C$_{47}$H$_{44}$NO$_8$[(M+H)$^+$]: 750.30669. Found: 750.30535.

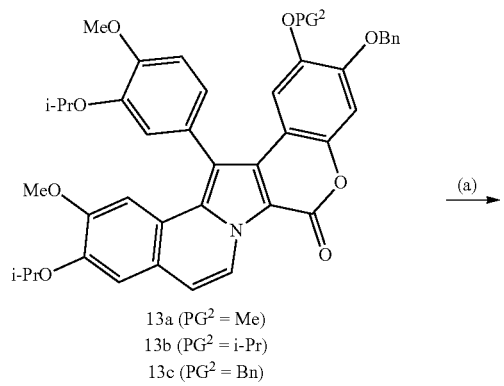

13a (PG$^2$ = Me)
13b (PG$^2$ = i-Pr)
13c (PG$^2$ = Bn)

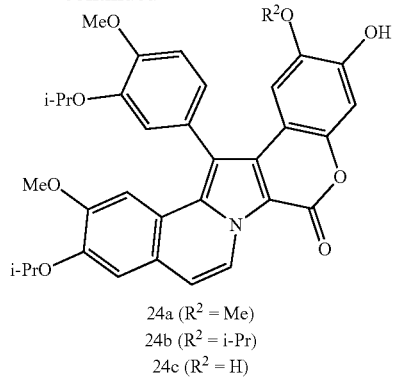

24a (R$^2$ = Me)
24b (R$^2$ = i-Pr)
24c (R$^2$ = H)

Step (a): Synthesis of Compound 24a

Under an argon atmosphere, to a solution of compound 13a (405 mg, 0.601 mmol) in ethyl acetate (15 mL) and ethanol (15 mL) were successively added palladium carbon (Pd: 10%, 80.8 mg) and ammonium formate (1.14 g, 18.0 mmol) and the mixture was heated under reflux for 1 hr. After allowing to cool, the reaction mixture was filtered through celite. The filtrate was concentrated, and the residue was purified by silica gel column chromatography (hexane: ethyl acetate=1:1) to give compound 24a as a pale-yellow solid (328 mg). yield 93%.

$^1$H NMR (400 MHz, CDCl$_3$): δ 1.36 (d, J=6.0 Hz, 3H), 1.37 (d, J=6.0 Hz, 3H), 1.43 (d, J=6.0 Hz, 6H), 3.45 (s, 3H), 3.51 (s, 3H), 3.97 (s, 3H), 4.57 (sep, J=6.0 Hz, 1H), 4.70 (sep, J=6.0 Hz, 1H), 5.95 (br s, 1H), 6.71 (s, 1H), 6.99 (s, 1H), 6.99 (d, J=7.3 Hz, 1H), 7.08 (s, 1H), 7.15 (d, J=8.1 Hz, 1H), 7.15 (d, J=1.7 Hz, 1H), 7.16 (s, 1H), 7.19 (dd, J=1.7 and 8.1 Hz, 1H), 9.18 (d, J=7.3 Hz, 1H).

HRDARTMS m/z. Calcd for C$_{34}$H$_{34}$NO$_8$[(M+H)$^+$]: 584.22844. Found: 584.22588.

Step (a): Synthesis of Compound 24b

Under an argon atmosphere, to a solution of compound 13b (84.9 mg, 0.121 mmol) in ethyl acetate (5 mL) and ethanol (5 mL) were successively added palladium carbon (Pd: 10%, 17 mg) and ammonium formate (233 mg, 3.70 mmol) and the mixture was heated under reflux for 30 min. After allowing to cool, the reaction mixture was filtered through celite. The filtrate was concentrated, and the residue was purified by silica gel column chromatography (acetone) to give compound 24b as a pale-yellow solid (71.2 mg). yield 97%.

$^1$H NMR (400 MHz, CDCl$_3$): δ 1.19 (d, J=6.0 Hz, 6H), 1.35 (d, J=6.0 Hz, 3H), 1.36 (d, J=6.0 Hz, 3H), 1.44 (d, J=6.0 Hz, 6H), 3.45 (s, 3H), 3.98 (s, 3H), 4.01 (sep, J=6.0 Hz, 1H), 4.55 (sep, J=6.0 Hz, 1H), 4.70 (sep, J=6.0 Hz, 1H), 5.92 (s, 1H), 6.68 (s, 1H), 6.99 (d, J=7.3 Hz, 1H), 6.99 (s, 1H), 7.09 (s, 1H), 7.12-7.17 (m, 3H), 7.17 (s, 1H), 9.18 (d, J=7.3 Hz, 1H).

HRDARTMS m/z. Calcd for C$_{36}$H$_{38}$NO$_8$[(M+H)$^+$]: 612.25974. Found: 612.26035.

Step (a): Synthesis of Compound 24c

Under an argon atmosphere, to a solution of compound 13c (200 mg, 0.267 mmol) in ethyl acetate (10 mL) and ethanol (10 mL) were successively added palladium carbon (Pd: 10%, 40 mg) and ammonium formate (505 mg, 8.01 mmol) and the mixture was heated under reflux for 1 hr. After allowing to cool, the reaction mixture was filtered through celite. The filtrate was concentrated, and the residue was purified by silica gel column chromatography (acetone) to give compound 24c as a pale-yellow solid (146 mg). yield 96%.

$^1$H NMR (500 MHz, DMSO-$d_6$): δ 1.21 (d, J=6.0 Hz, 3H), 1.25 (d, J=6.0 Hz, 3H), 1.31 (d, J=6.0 Hz, 6H), 3.33 (s, 3H), 3.89 (s, 3H), 4.58 (sep, J=6.0 Hz, 1H), 4.74 (sep, J=6.0 Hz, 1H), 6.74 (s, 1H), 6.84 (s, 1H), 6.90 (s, 1H), 7.08-7.12 (m, 2H), 7.26 (d, J=7.3 Hz, 1H), 7.27 (d, J=8.4 Hz, 1H), 7.41 (s, 1H), 9.04 (br s, 1H), 9.08 (d, J=7.3 Hz, 1H), 9.76 (br s, 1H).

HRDARTMS m/z. Calcd for $C_{33}H_{32}NO_8[(M+H)^+]$: 570.21279. Found: 570.21008.

J=1.8 Hz, 1H), 7.16 (d, J=8.2 Hz, 1H), 7.18 (s, 1H), 7.21 (dd, J=1.8 and 8.2 Hz, 1H), 9.18 (d, J=7.4 Hz, 1H).

HRDARTMS m/z. Calcd for $C_{39}H_{45}N_2O_8[(M+H)^+]$: 669.31759. Found: 669.31472.

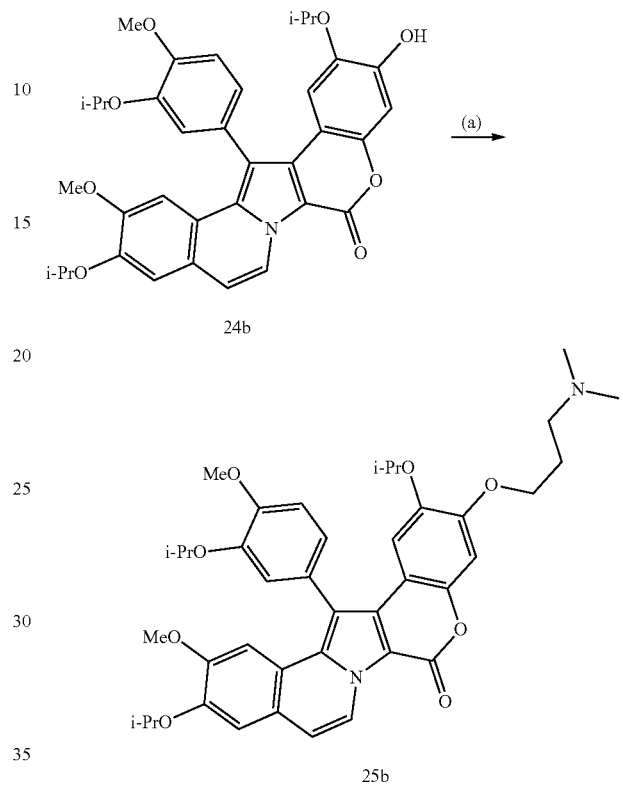

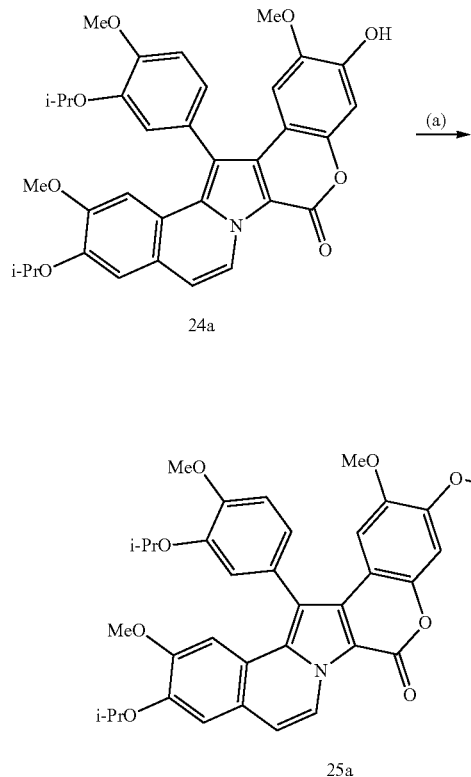

Step (a): Synthesis of Compound 25a

Under an argon atmosphere, to a solution of compound 24a (150 mg, 0.257 mmol) in dry acetone (7 mL) were successively added 3-(dimethylamino)propyl chloride hydrochloride (48.7 mg, 0.308 mmol) and potassium carbonate (178 mg, 1.29 mmol), and the mixture was heated under reflux for 24 hr. After allowing to cool, saturated aqueous sodium hydrogen carbonate solution was added and the mixture was concentrated under reduced pressure. Water was added to the residue and the mixture was extracted with dichloromethane. The extract was washed successively with water and saturated brine and dried over anhydrous sodium sulfate, and dichloromethane was evaporated under reduced pressure. The residue was purified by CHROMATOREX NH-DM1020 column chromatography (hexane:ethyl acetate=3:2) to give compound 25a as a pale-yellow solid (120 mg). yield 70%.

$^1$H NMR (400 MHz, CDCl$_3$): δ 1.36 (d, J=6.1 Hz, 3H), 1.36 (d, J=6.1 Hz, 3H), 1.43 (d, J=6.1 Hz, 6H), 2.01 (quin, J=7.0 Hz, 2H), 2.25 (s, 6H), 2.44 (t, J=7.0 Hz, 2H), 3.45 (s, 3H), 3.47 (s, 3H), 3.97 (s, 3H), 4.07 (t, J=7.0 Hz, 2H), 4.56 (sep, J=6.1 Hz, 1H), 4.69 (sep, J=6.1 Hz, 1H), 6.74 (s, 1H), 6.94 (s, 1H), 7.00 (d, J=7.4 Hz, 1H), 7.09 (s, 1H), 7.16 (d,

Step (a): Synthesis of Compound 25b

Under an argon atmosphere, to a solution of compound 24b (30.0 mg, 49.0 μmol) in dry acetone (2 mL) were successively added 3-(dimethylamino)propyl chloride hydrochloride (9.3 mg, 58.8 μmol) and potassium carbonate (40.6 mg, 0.294 mmol), and the mixture was heated under reflux for 21 hr. After allowing to cool, saturated aqueous sodium hydrogen carbonate solution was added and the mixture was concentrated under reduced pressure. Water was added to the residue and the mixture was extracted with dichloromethane. The extract was washed successively with water and saturated brine and dried over anhydrous sodium sulfate, and dichloromethane was evaporated under reduced pressure. The residue was purified by silica gel column chromatography (hexane:ethyl acetate=1:1-dichloromethane:methanol=1:1) to give compound 25b as a pale-yellow solid (11.6 mg). yield 34%.

$^1$H NMR (400 MHz, CDCl$_3$): δ 1.17 (d, J=6.1 Hz, 3H), 1.17 (d, J=6.1 Hz, 3H), 1.34 (d, J=6.1 Hz, 3H), 1.35 (d, J=6.1 Hz, 3H), 1.43 (d, J=6.1 Hz, 6H), 2.00 (quin, J=6.8 Hz, 2H), 2.25 (s, 6H), 2.47 (t, J=7.3 Hz, 2H), 3.44 (s, 3H), 3.97 (s, 3H), 3.97 (sep, J=6.1 Hz, 1H), 4.07 (t, J=6.4 Hz, 2H), 4.53 (sep, J=6.1 Hz, 1H), 4.70 (sep, J=6.1 Hz, 1H), 6.76 (s, 1H), 6.96 (s, 1H), 7.02 (d, J=7.4 Hz, 1H), 7.10 (s, 1H), 7.11 (s, 1H), 7.14 (s, 2H), 7.17 (s, 1H), 9.22 (d, J=7.4 Hz, 1H).

HRDARTMS m/z. Calcd for $C_{41}H_{49}N_2O_8[(M+H)^+]$: 697.34889. Found: 697.35000.

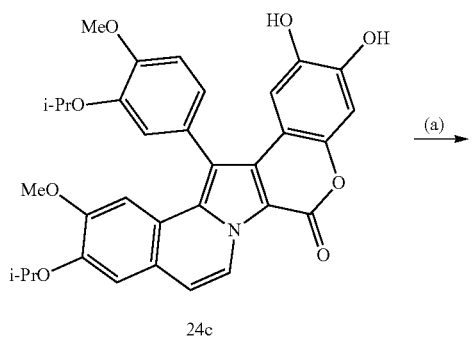

24c

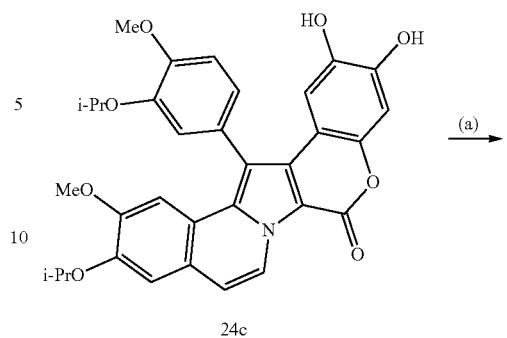

24c

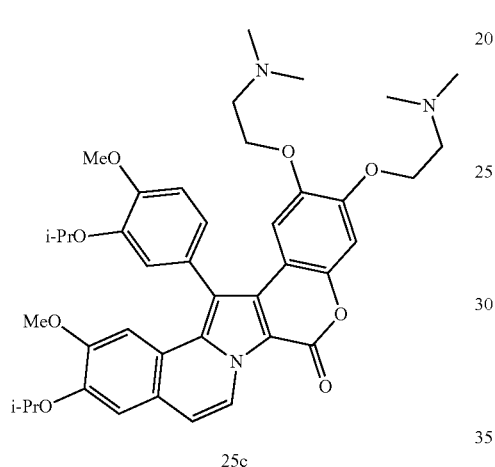

25c

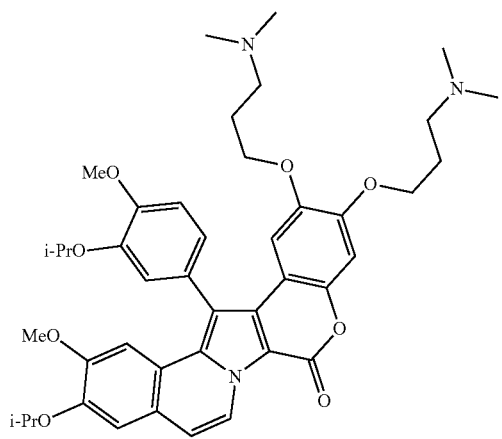

25d

Step (a): Synthesis of Compound 25c

Under an argon atmosphere, to a solution of compound 24c (40.3 mg, 70.8 μmol) in dry acetone (10 mL) were successively added 2-(dimethylamino)ethyl chloride hydrochloride (51.0 mg, 0.354 mmol), sodium iodide (10.0 mg, 66.7 μmol), and potassium carbonate (147 mg, 1.06 mmol), and the mixture was heated under reflux for 10 hr. After allowing to cool, 2-(dimethylamino)ethyl chloride hydrochloride (51.0 mg, 0.354 mmol) and potassium carbonate (147 mg, 1.06 mmol) were added, and the mixture was further heated under reflux for 12 hr. After allowing to cool, the mixture was diluted with dichloromethane and filtered through celite. The filtrate was concentrated under reduced pressure, and the residue was purified by CHROMATOREX NH-DM1020 column chromatography (hexane:ethyl acetate=1:2-ethyl acetate) to give compound 25c as a pale-yellow solid (27.0 mg). yield 54%.

$^1$H NMR (500 MHz, CDCl$_3$): δ 1.34 (d, J=6.1 Hz, 3H), 1.34 (d, J=6.1 Hz, 3H), 1.43 (d, J=6.1 Hz, 6H), 2.28 (s, 6H), 2.34 (s, 6H), 2.55-2.65 (m, 2H), 2.78 (t, J=5.8 Hz, 2H), 3.44 (s, 3H), 3.67 (t, J=5.8 Hz, 2H), 3.96 (s, 3H), 4.12 (t, J=5.8 Hz, 2H), 4.53 (sep, J=6.1 Hz, 1H), 4.70 (sep, J=6.1 Hz, 1H), 6.76 (s, 1H), 6.96 (s, 1H), 7.02 (d, J=7.4 Hz, 1H), 7.10 (s, 1H), 7.11 (d, J=1.8 Hz, 1H), 7.15 (d, J=8.1 Hz, 1H), 7.17 (s, 1H), 7.18 (dd, J=1.8 and 8.1 Hz, 1H), 9.22 (d, J=7.4 Hz, 1H).

HRDARTMS m/z. Calcd for $C_{41}H_{50}N_3O_8[(M+H)^+]$: 712.35979. Found: 712.36040.

Step (a): Synthesis of Compound 25d

Under an argon atmosphere, to a solution of compound 24c (146 mg, 0.256 mmol) in dry acetone (25 mL) were successively added 3-(dimethylamino)propyl chloride hydrochloride (194 mg, 1.23 mmol) and potassium carbonate (708 mg, 5.12 mmol), and the mixture was heated under reflux for 48 hr. After allowing to cool, saturated aqueous sodium hydrogen carbonate solution was added and the mixture was concentrated under reduced pressure. Water was added to the residue and the mixture was extracted with dichloromethane. The extract was washed successively with water and saturated brine and dried over anhydrous sodium sulfate, and dichloromethane was evaporated under reduced pressure. The residue was recrystallized from dichloromethane-hexane to give compound 25d as a pale-brown solid (134 mg). yield 71%.

$^1$H NMR (400 MHz, CDCl$_3$): δ 1.34 (d, J=6.1 Hz, 3H), 1.35 (d, J=6.1 Hz, 3H), 1.43 (d, J=6.1 Hz, 6H), 1.81 (quin, J=6.9 Hz, 2H), 2.00 (quin, J=6.8 Hz, 2H), 2.23 (s, 6H), 2.25 (s, 6H), 2.31-2.41 (m, 2H), 2.47 (t, J=7.3 Hz, 2H), 3.44 (s, 3H), 3.62 (t, J=6.3 Hz, 2H), 3.97 (s, 3H), 4.08 (t, J=6.5 Hz, 2H), 4.53 (sep, J=6.1 Hz, 1H), 4.70 (sep, J=6.1 Hz, 1H), 6.75 (s, 1H), 6.96 (s, 1H), 7.01 (d, J=7.3 Hz, 1H), 7.09 (s, 1H), 7.11 (d, J=1.8 Hz, 1H), 7.14 (d, J=8.1 Hz, 1H), 7.16 (s, 1H), 7.18 (dd, J=1.8 and 8.1 Hz, 1H), 9.22 (d, J=7.3 Hz, 1H).

HRDARTMS m/z. Calcd for $C_{43}H_{54}N_3O_8[(M+H)^+]$: 740.39109. Found: 740.39380.

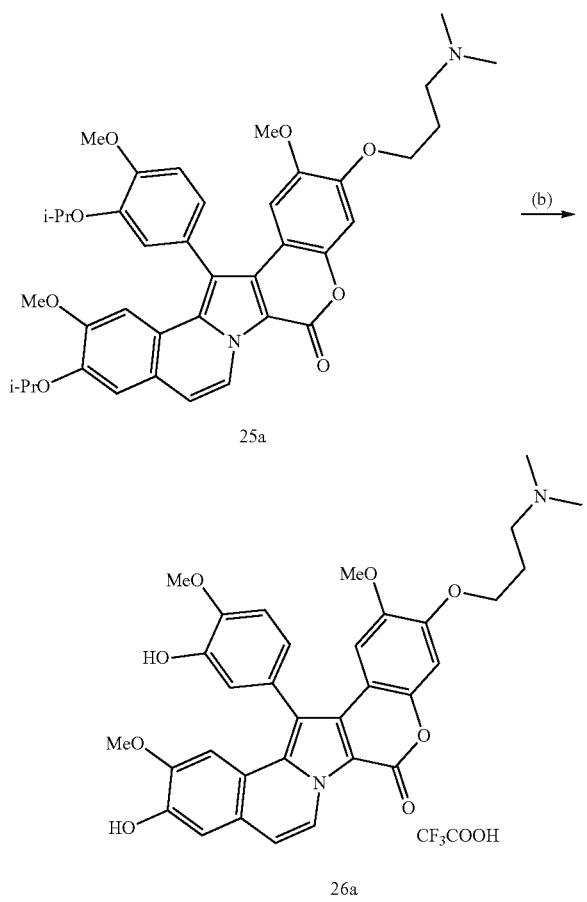

25a

26a

Step (b): Synthesis of Compound 26a

Under an argon atmosphere, to a solution of compound 25a (60.0 mg, 89.7 μmol) in dry dichloromethane (4.0 mL) was added dropwise a nitrobenzene solution of aluminum chloride (1.0 M, 540 μL, 0.540 mmol) at room temperature, and the mixture was stirred at the same temperature for 18 hr. To the reaction solution was added a mixed solution of sodium hydrogen carbonate (200 mg, 2.38 mmol) and Rochelle salt (440 mg, 1.56 mmol) in water (7.0 mL). After vigorously stirring for 1 hr, dichloromethane and water were evaporated under reduced pressure. Water was added to the residue and nitrobenzene was removed azeotropically under reduced pressure. Water was added to the residue and the mixture was sufficiently suspended. The solid was collected by suction filtration and dried under reduced pressure to give a deprotected product as a pale-gray solid (47.5 mg). yield 91%.

$^1$H NMR (500 MHz, DMSO-d$_6$): δ 1.85 (quin, J=6.8 Hz, 2H), 2.14 (s, 6H), 2.34 (t, J=7.1 Hz, 2H), 3.39 (s, 3H), 3.40 (s, 3H), 3.87 (s, 3H), 4.04 (t, J=6.5 Hz, 2H), 6.78 (s, 1H), 7.00-7.04 (m, 2H), 7.08 (s, 1H), 7.19 (s, 1H), 7.21 (s, 1H), 7.22 (d, J=7.3 Hz, 1H), 7.24 (d, J=8.7 Hz, 1H), 9.00 (d, J=7.3 Hz, 1H), 9.39 (br s, 1H).

To a suspension of the deprotected product (20.0 mg, 34.2 μmol) in dichloromethane (1.0 mL) was added trifluoroacetic acid (1.0 mL), and the mixture was stirred at room temperature for 30 min. The solvent was evaporated under reduced pressure and the residue was purified by column chromatography (Sephadex LH-20, 0.1% v/v trifluoroacetic acid-containing methanol) to give compound 26a as a brown solid (21.6 mg). yield 90%.

$^1$H NMR (500 MHz, DMSO-d$_6$): δ 2.13 (quin, J=6.9 Hz, 2H), 2.82 (s, 3H), 2.83 (s, 3H), 3.21 (quin, J=5.1 Hz, 2H), 3.40 (s, 3H), 3.40 (s, 3H), 3.88 (s, 3H), 4.13 (t, J=6.1 Hz, 2H), 6.81 (s, 1H), 7.00-7.04 (m, 2H), 7.17 (s, 1H), 7.19 (s, 1H), 7.21 (s, 1H), 7.25 (d, J=7.3 Hz, 1H), 7.25 (d, J=9.2 Hz, 1H), 9.01 (d, J=7.3 Hz, 1H), 9.43 (br s, 2H), 9.98 (br s, 1H).

HRDARTMS m/z. Calcd for C$_{33}$H$_{33}$N$_2$O$_8$[(M-CF$_3$COO)$^+$]: 585.22369. Found: 585.22208.

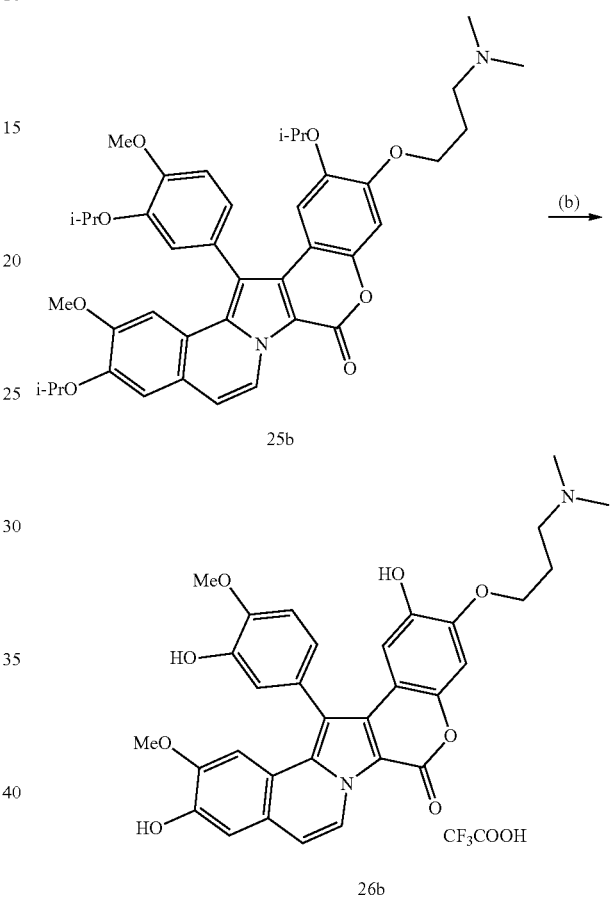

25b

26b

Step (b): Synthesis of Compound 26b

Under an argon atmosphere, to a solution of compound 25b (20.0 mg, 28.7 μmol) in dry dichloromethane (5.0 mL) was added dropwise a nitrobenzene solution of aluminum chloride (1.0 M, 218 μL, 0.218 mmol) at room temperature, and the mixture was stirred at the same temperature for 48 hr. To the reaction solution was added a mixed solution of sodium hydrogen carbonate (55.0 mg, 0.654 mmol) and Rochelle salt (185 mg, 0.654 mmol) in water (3.3 mL). After vigorously stirring for 1 hr, dichloromethane and water were evaporated under reduced pressure. Water was added to the residue and nitrobenzene was removed azeotropically under reduced pressure and the residue was dried under reduced pressure. Dichloromethane (2.0 mL) and trifluoroacetic acid (2.0 mL) were added to the residue, and the solvent was evaporated under reduced pressure. The residue was purified by column chromatography (Sephadex LH-20, 0.1% v/v trifluoroacetic acid-containing water—0.1% v/v trifluoroacetic acid-containing water:methanol=1:1-0.1% v/v trifluoroacetic acid-containing methanol) to give compound 26b as a brown solid (19.3 mg). yield 98%.

¹H NMR (500 MHz, DMSO-d₆): δ 2.12 (quin, J=5.5 Hz, 2H), 2.82 (s, 6H), 3.28 (t, J=7.8 Hz, 2H), 3.37 (s, 3H), 3.90 (s, 3H), 4.12 (t, J=5.9 Hz, 2H), 6.81 (s, 1H), 6.92 (s, 1H), 6.94 (d, J=2.0 Hz, 1H), 6.95 (dd, J=2.0 and 8.0 Hz, 1H), 7.11 (s, 1H), 7.18 (s, 1H), 7.21 (d, J=7.4 Hz, 1H), 7.23 (d, J=8.0 Hz, 1H), 9.03 (d, J=7.4 Hz, 1H), 9.04 (br s, 1H), 9.41 (br s, 1H), 9.53 (br s, 1H), 9.98 (br s, 1H).

HRDARTMS m/z. Calcd for $C_{32}H_{31}N_2O_8[(M-CF_3COO)^+]$: 571.20804. Found: 571.20608.

¹H NMR (500 MHz, DMSO-d₆): δ 2.82 (s, 6H), 2.88 (s, 6H), 3.40 (s, 3H), 3.54 (t, J=4.8 Hz, 2H), 3.90 (s, 3H), 3.90-3.98 (m, 2H), 4.44 (t, J=5.0 Hz, 2H), 6.87 (s, 1H), 7.01 (d, J=2.1 Hz, 1H), 7.03 (dd, J=2.1 and 8.1 Hz, 1H), 7.14 (s, 1H), 7.21 (s, 1H), 7.25 (d, J=8.1 Hz, 1H), 7.27 (d, J=7.4 Hz, 1H), 7.35 (s, 1H), 9.02 (d, J=7.4 Hz, 1H), 9.48 (br s, 1H), 10.04 (br s, 3H).

HRDARTMS m/z. Calcd for $C_{35}H_{38}N_3O_8[(M-2CF_3COO-H)^+]$: 628.26589. Found: 628.26746.

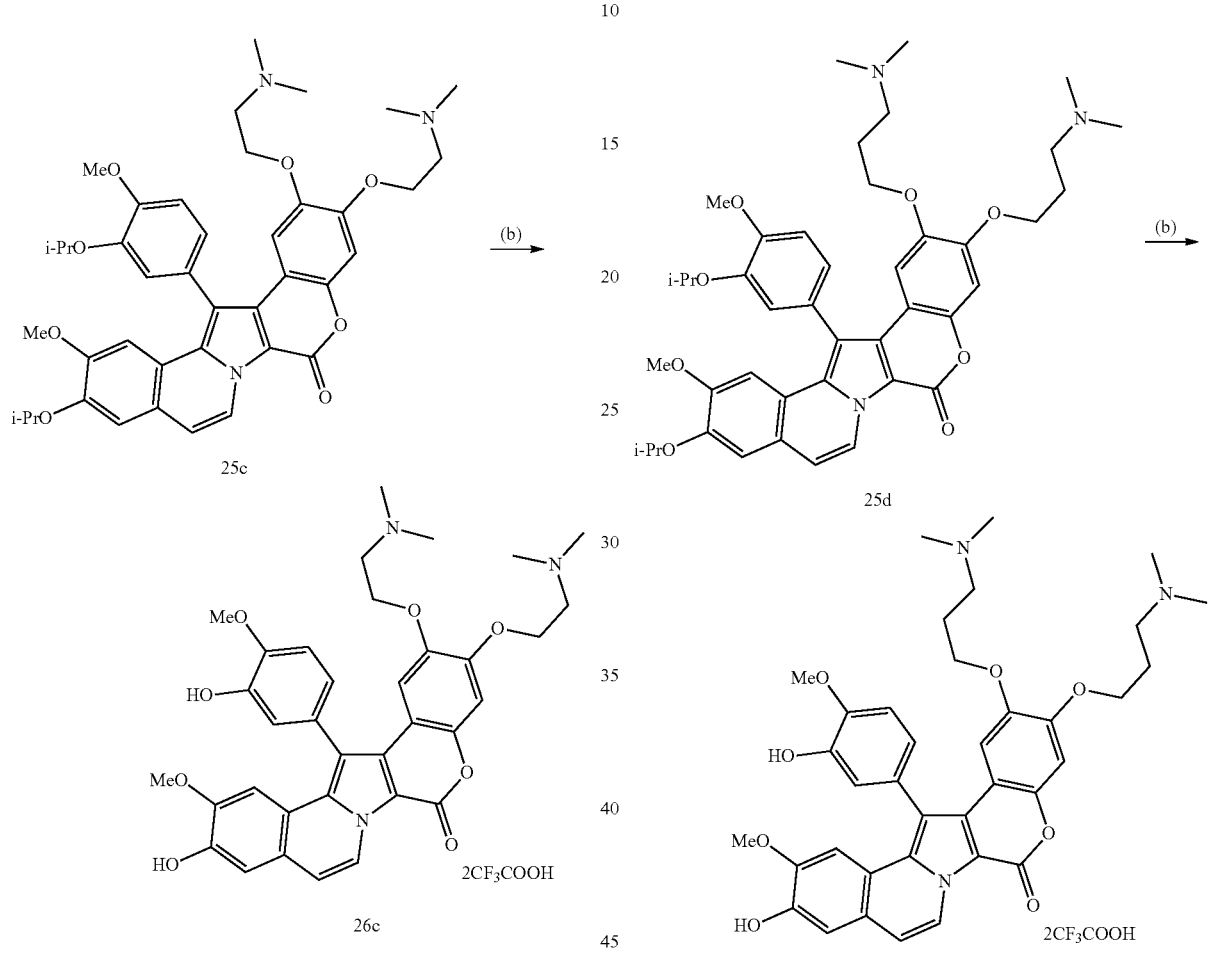

Step (b): Synthesis of Compound 26c

Under an argon atmosphere, to a solution of compound 25c (13.4 mg, 18.8 μmol) in dry dichloromethane (1.0 mL) was added dropwise a nitrobenzene solution of aluminum chloride (1.0 M, 120 μL, 0.120 mmol) at room temperature and the mixture was stirred at the same temperature for 48 hr. To the reaction solution was added a mixed solution of sodium hydrogen carbonate (30.3 mg, 0.361 mmol) and Rochelle salt (102 mg, 0.361 mmol) in water (0.7 mL). After vigorously stirring for 1 hr, dichloromethane and water were evaporated under reduced pressure. Water was added to the residue and nitrobenzene was removed azeotropically under reduced pressure. Water was added to the residue and the mixture was sufficiently suspended. The solid was collected by suction filtration. To a suspension of the obtained solid in dichloromethane (1.0 mL) was added trifluoroacetic acid (1.0 mL), and the solvent was evaporated under reduced pressure. The residue was purified by column chromatography (Sephadex LH-20, 0.1% v/v trifluoroacetic acid-containing methanol) to give compound 26c as a brown solid (15.0 mg). yield 93%.

Step (b): Synthesis of Compound 26d

Under an argon atmosphere, to a solution of compound 25d (90.2 mg, 0.122 mmol) in dry dichloromethane (19.5 mL) was added dropwise a nitrobenzene solution of aluminum chloride (1.0 M, 780 μL, 0.780 mmol) at room temperature, and the mixture was stirred at the same temperature for 84.5 hr. To the reaction solution was added a mixed solution of sodium hydrogen carbonate (166 mg, 1.97 mmol) and Rochelle salt (557 mg, 1.97 mmol) in water (3.9 mL). After vigorously stirring for 1 hr, dichloromethane and water were evaporated under reduced pressure. Water was added to the residue, and nitrobenzene was removed azeotropically under reduced pressure. Water was added to the residue and the mixture was sufficiently suspended. The solid was collected by suction filtration and dried under reduced pressure to give a deprotected product as a brown solid (80.0 mg). yield 100%.

¹H NMR (500 MHz, DMSO-d₆): δ 1.63-1.70 (m, 2H), 1.82-1.89 (m, 2H), 2.14 (s, 6H), 2.17 (s, 6H), 2.23-2.30 (m,

2H), 2.36-2.43 (m, 2H), 3.39 (s, 3H), 3.53-3.60 (m, 2H), 3.88 (s, 3H), 4.01-4.08 (m, 2H), 6.76 (s, 1H), 6.97-7.02 (m, 2H), 7.07 (s, 1H), 7.15 (s, 1H), 7.19 (s, 1H), 7.20-7.24 (m, 2H), 8.99 (d, J=7.3 Hz, 1H).

To a suspension of the deprotected product (78.3 mg, 0.106 mmol) in dichloromethane (3.0 mL) was added trifluoroacetic acid (3.0 mL), and the mixture was stirred at room temperature for 30 min. The solvent was evaporated under reduced pressure and the residue was purified by column chromatography (Sephadex LH-20, 0.1% v/v trifluoroacetic acid-containing methanol) to give compound 26d as a brown solid (94.2 mg). yield 100%.

$^1$H NMR (500 MHz, DMSO-$d_6$): δ 1.92-2.00 (m, 2H), 2.09-2.17 (m, 2H), 2.81 (s, 6H), 2.83 (s, 6H), 3.06-3.13 (m, 2H), 3.21 (t, J=7.2 Hz, 2H), 3.40 (s, 3H), 3.59-3.70 (m, 2H), 3.90 (s, 3H), 4.13 (t, J=6.2 Hz, 2H), 6.79 (s, 1H), 7.01 (d, J=2.0 Hz, 1H), 7.02 (dd, J=2.0 and 8.0 Hz, 1H), 7.17 (s, 1H), 7.19 (s, 1H), 7.21 (s, 1H), 7.25 (d, J=7.4 Hz, 1H), 7.26 (d, J=8.0 Hz, 1H), 9.00 (d, J=7.4 Hz, 1H), 9.50 (br s, 1H), 9.84 (br s, 1H), 9.87 (br s, 1H), 10.05 (br s, 1H).

HRDARTMS m/z. Calcd for $C_{37}H_{42}N_3O_8[(M-2CF_3COO-H)^+]$: 656.29719. Found: 656.29442.

[Synthesis Method of Azalamellarin N Derivatives]

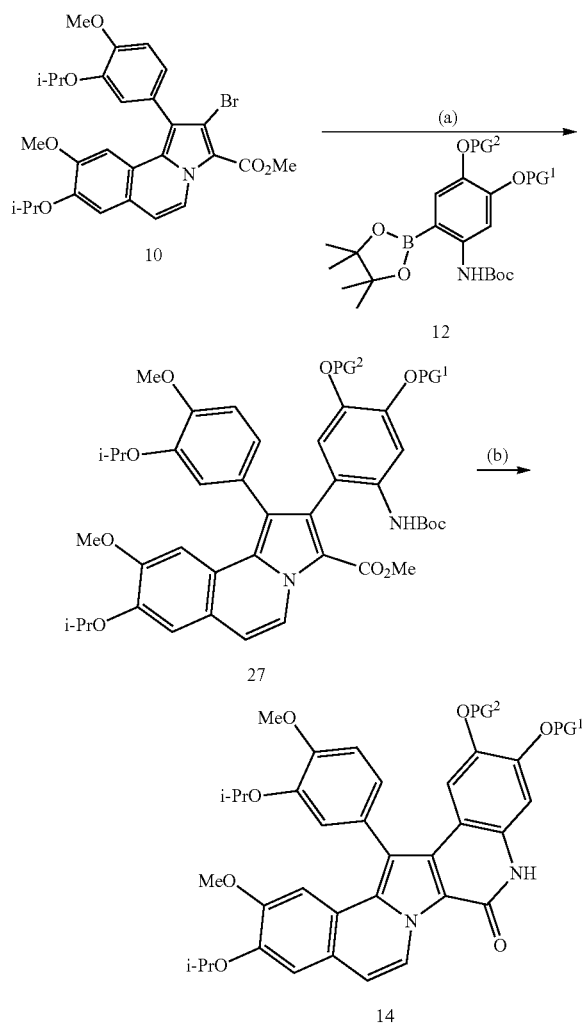

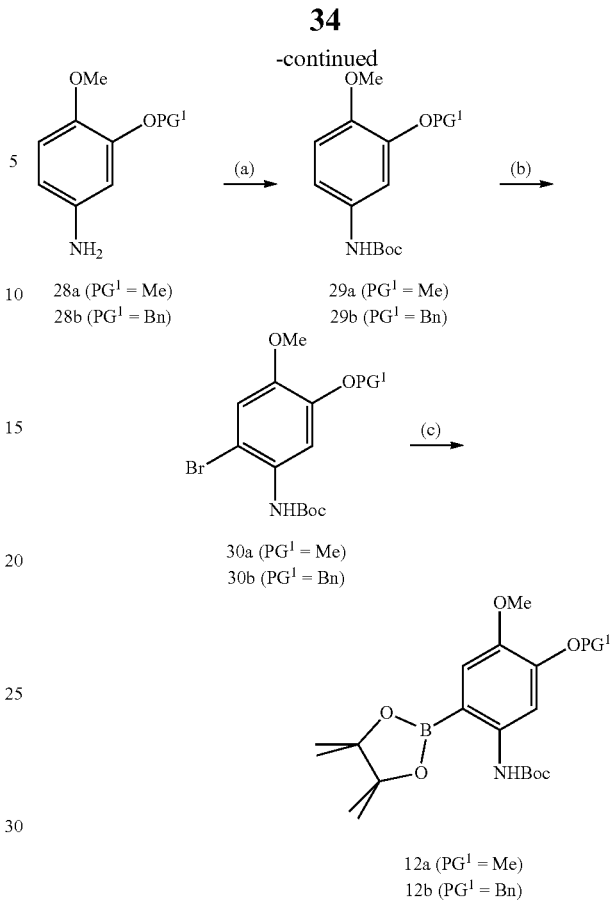

Step (a): Synthesis of Compound 29a

Under an argon atmosphere, to a solution of compound 28a (4.33 g, 28.3 mmol), which was commercially available or synthesized by a method known per se or a method analogous thereto, in dry tetrahydrofuran (120 mL) was added dropwise di-tert-butyl dicarbonate (7.20 mL, 31.2 mmol) at room temperature, and the mixture was heated under reflux for 2 hr. After allowing to cool, the solvent was evaporated under reduced pressure. The residue was recrystallized from ether to give compound 29a as a pale-brown solid (6.68 g). yield 93%.

$^1$H NMR (400 MHz, CDCl$_3$): δ 1.51 (s, 9H), 3.84 (s, 3H), 3.87 (s, 3H), 6.47 (br s, 1H), 6.72 (dd, J=2.2 and 8.6 Hz, 1H), 6.78 (d, J=8.6 Hz, 1H), 7.18 (br, 1H).

HRDARTMS m/z. Calcd for $C_{13}H_{20}NO_4[(M+H)^+]$: 254.1392. Found: 254.1399.

Step (a): Synthesis of Compound 29b

According to the procedure described for the synthesis of compound 28a, compound 28b (6.87 g, 30.0 mmol), which was commercially available or synthesized by a method known per se or a method analogous thereto, was reacted. The mixture was purified by silica gel flash chromatography (hexane:ethyl acetate=4:1) to give compound 29b as a pale-brown solid (3.10 g). yield 31%.

$^1$H NMR (400 MHz, CDCl$_3$): δ 1.50 (s, 9H), 3.83 (s, 3H), 5.12 (s, 2H), 6.37 (br s, 1H), 6.81 (s, 2H), 7.12 (br s, 1H), 7.27-7.32 (m, 1H), 7.33-7.39 (m, 2H), 7.42-7.47 (m, 2H).

HRDARTMS m/z. Calcd for $C_{19}H_{23}BrNO_4(M^+)$: 329.1627. Found: 329.1639.

Step (b): Synthesis of Compound 30a

Under an argon atmosphere, to a solution of compound 29a (333 mg, 1.31 mmol) in dry tetrahydrofuran (5 mL) was added N-bromosuccinimide (254 mg, 1.43 mmol) at 0° C.

After stirring at 0° C. for 1 hr, water was added and the mixture was allowed to warm to room temperature. The mixture was extracted with dichloromethane and the extract was washed successively with water and saturated brine and dried over anhydrous sodium sulfate. Dichloromethane was evaporated under reduced pressure. The residue was purified by silica gel column chromatography (hexane:ethyl acetate=10:1) to give compound 30a as a pale-yellow solid (377 mg). yield 87%.

$^{1}$H NMR (300 MHz, CDCl$_3$): δ 1.53 (s, 9H), 3.84 (s, 3H), 3.91 (s, 3H), 6.79 (br s, 1H), 6.97 (s, 1H), 7.81 (br s, 1H).

HRDARTMS m/z. Calcd for C$_{13}$H$_{18}$BrNO$_4$(M$^+$): 331.0419. Found: 331.0425.

Step (b): Synthesis of Compound 30b

According to the procedure described for the synthesis of compound 30a, compound 29b (3.00 g, 9.11 mmol) was reacted. The mixture was purified by silica gel flash chromatography (hexane:ethyl acetate=3:1) to give compound 30b as a pale-yellow solid (3.38 g). yield 91%.

$^{1}$H NMR (400 MHz, CDCl$_3$): δ 1.53 (s, 9H), 3.82 (s, 3H), 5.13 (s, 2H), 6.75 (br s, 1H), 6.99 (s, 1H), 7.28-7.33 (m, 1H), 7.34-7.39 (m, 2H), 7.45-7.50 (m, 2H), 7.90 (br s, 1H).

HRDARTMS m/z. Calcd for C$_{19}$H$_{22}$BrNO$_4$(M$^+$): 407.0732. Found: 409.0743.

Step (c): Synthesis of Compound 12a

Under an argon atmosphere, to a solution of compound 30a (377 mg, 1.13 mmol) and [1,1'-bis(diphenylphosphino)ferrocene]palladium(II) dichloride dichloromethane adduct (46.9 mg, 57.4 μmol) in 1,4-dioxane (6.0 mL) were successively added triethylamine (640 μL, 4.54 mmol) and pinacolborane (490 μL, 3.40 mmol) at room temperature, and the mixture was heated under reflux for 2.5 hr. After allowing to cool, saturated aqueous ammonium chloride solution was added and the solvent was evaporated. Water was added to the residue and the mixture was extracted with dichloromethane. The extract was washed successively with water and saturated brine and dried over anhydrous sodium sulfate. Dichloromethane was evaporated under reduced pressure. The residue was purified by silica gel column chromatography (hexane:ethyl acetate=50:1) to give compound 12a as a pale-yellow solid (282 mg). yield 65%.

$^{1}$H NMR (400 MHz, CDCl$_3$): δ 1.35 (s, 12H), 1.52 (s, 9H), 3.88 (s, 3H), 3.94 (s, 3H), 7.15 (s, 1H), 7.92 (br s, 1H), 8.67 (br s, 1H).

HRDARTMS m/z. Calcd for C$_{19}$H$_{30}$BNO$_6$(M$^+$): 379.2166. Found: 379.2169.

Step (c): Synthesis of Compound 12b

According to the procedure described for the synthesis of compound 12a, compound 30b (3.38 g, 8.28 mmol) was reacted. The mixture was purified by silica gel flash chromatography (hexane:ethyl acetate=5:1) to give compound 12b as a pale-yellow solid (2.72 g). yield 72%.

$^{1}$H NMR (300 MHz, CDCl$_3$): δ 1.35 (s, 12H), 1.52 (s, 9H), 3.86 (s, 3H), 5.19 (s, 2H), 7.18 (s, 1H), 7.27-7.32 (m, 1H), 7.33-7.39 (m, 2H), 7.47-7.51 (m, 2H), 8.02 (br s, 1H), 8.63 (br s, 1H).

HRDARTMS m/z. Calcd for C$_{25}$H$_{34}$BNO$_6$(M$^+$): 455.2479. Found: 455.2485.

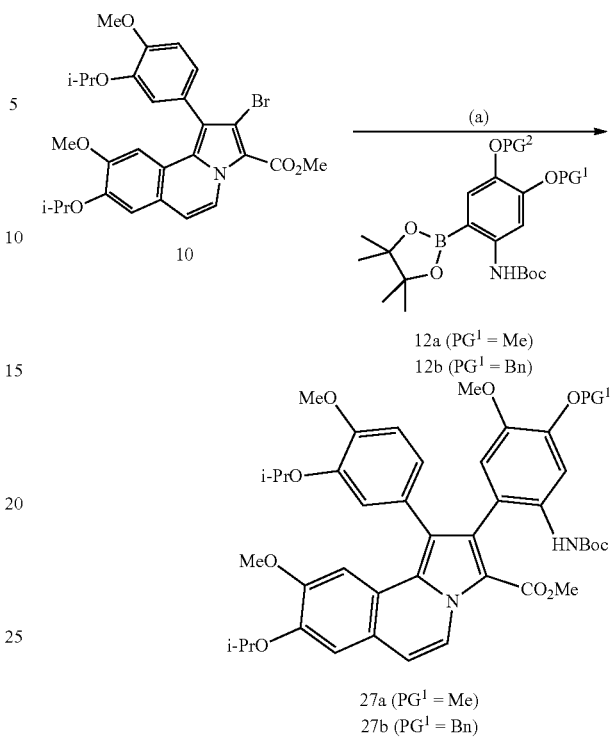

Step (a): Synthesis of Compound 27a

Under an argon atmosphere, a mixture of compound 10 (100 mg, 0.180 mmol), compound 12a (114 mg, 0.301 mmol), Pd(PPh$_3$)$_4$ (23.2 mg, 20.1 μmol), Na$_2$CO$_3$ (141 mg, 1.32 mmol), 1,2-dimethoxyethane (5.0 mL), and degassed water (0.5 mL) was stirred in a sealed tube with heating at 85° C. for 24 hr. After allowing to cool, the solvent was evaporated under reduced pressure. Water was added to the residue and the mixture was extracted with dichloromethane. The extract was washed successively with water and saturated brine and dried over anhydrous sodium sulfate, and dichloromethane was evaporated under reduced pressure. The residue was purified by silica gel column chromatography (hexane:ethyl acetate=3:1-2:1-1:1-ethyl acetate) to give compound 27a as a pale-yellow semisolid (115 mg). yield 88%.

$^{1}$H NMR (500 MHz, DMSO-d$_6$): δ 1.02 (d, J=6.1 Hz, 1.72H), 1.09 (d, J=6.1 Hz, 1.72H), 1.11 (d, J=6.1 Hz, 1.28H), 1.16 (d, J=6.1 Hz, 1.28H), 1.30 (d, J=6.1 Hz, 6H), 1.37 (s, 9H), 3.29 (s, 1.28H), 3.29 (s, 1.72H), 3.48 (s, 1.72H), 3.53 (s, 1.28H), 3.53 (s, 1.72H), 3.56 (s, 1.28H), 3.69 (s, 1.72H), 3.70 (s, 1.28H), 3.71 (s, 1.28H), 3.74 (s, 1.72H), 4.26 (sep, J=6.1 Hz, 0.57H), 4.43 (sep, J=6.1 Hz, 0.43H), 4.70 (sep, J=6.1 Hz, 1H), 6.52 (s, 0.57H), 6.71 (s, 0.43H), 6.85-7.17 (m, 4H), 7.18 (d, J=7.6 Hz, 0.57H), 7.18 (d, J=7.6 Hz, 0.43H), 7.34 (s, 1H), 7.35 (br s, 0.43H), 7.44 (br s, 0.57H), 7.60 (br s, 0.43H), 7.85 (br s, 0.57H), 9.20 (d, J=7.6 Hz, 0.57H), 9.23 (d, J=7.6 Hz, 0.43H).

HRDARTMS m/z. Calcd for C$_{41}$H$_{49}$N$_2$O$_{10}$[(M+H)$^+$]: 729.3387. Found: 729.3358.

Step (a): Synthesis of Compound 27b

According to the procedure described for the synthesis of compound 27a, compound 10 (100 mg, 0.180 mmol) and compound 12b (137 mg, 0.302 mmol) were reacted. The mixture was purified by silica gel column chromatography (hexane:ethyl acetate=3:1-2:1-1:1-1:2) to give compound 27b as a pale-yellow semisolid (131 mg). yield 91%.

¹H NMR (500 MHz, DMSO-d₆): δ 1.02 (d, J=6.1 Hz, 1.67H), 1.10 (d, J=6.1 Hz, 1.67H), 1.13 (d, J=6.1 Hz, 1.33H), 1.17 (d, J=6.1 Hz, 1.33H), 1.30 (d, J=6.1 Hz, 6H), 1.37 (s, 9H), 3.29 (s, 1.33H), 3.30 (s, 1.67H), 3.49 (s, 1.67H), 3.53 (s, 1.33H), 3.54 (s, 1.67H), 3.57 (s, 1.33H), 3.72 (s, 1.33H), 3.74 (s, 1.67H), 4.28 (sep, J=6.1 Hz, 0.56H), 4.44 (sep, J=6.1 Hz, 0.44H), 4.71 (sep, J=6.1 Hz, 1H), 4.92-5.01 (m, 2H), 6.56 (s, 0.56H), 6.75 (s, 0.44H), 6.86-7.10 (m, 4H), 7.18 (d, J=7.6 Hz, 0.56H), 7.19 (d, J=7.6 Hz, 0.44H), 7.23-7.47 (m, 7H), 7.64 (br s, 0.44H), 7.89 (br s, 0.56H), 9.21 (d, J=7.6 Hz, 0.56H), 9.23 (d, J=7.6 Hz, 0.44H).

HRDARTMS m/z. Calcd for $C_{47}H_{53}N_2O_{10}[(M+H)^+]$: 805.3700. Found: 805.3715.

Step (a): Synthesis of Compound 14b

According to the procedure described for the synthesis of compound 14a, compound 27b (100 mg, 0.180 mmol) was reacted. As a result, compound 14b was obtained as a pale-brown solid (78.2 mg). yield 85%.

¹H NMR (500 MHz, CDCl₃): δ 1.34 (d, J=6.1 Hz, 3H), 1.34 (d, J=6.1 Hz, 3H), 1.43 (d, J=6.1 Hz, 3H), 1.44 (d, J=6.1 Hz, 3H), 3.42 (s, 3H), 3.46 (s, 3H), 3.93 (s, 3H), 4.53 (sep, J=6.1 Hz, 1H), 4.68 (sep, J=6.1 Hz, 1H), 5.22 (s, 2H), 6.76-6.88 (m, 2H), 7.00-7.30 (m, 9H), 7.43-7.47 (m, 2H), 9.44 (br s, 1H), 11.05 (br s, 1H).

HRDARTMS m/z. Calcd for $C_{41}H_{41}N_2O_7[(M+H)^+]$: 673.2914. Found: 673.2939.

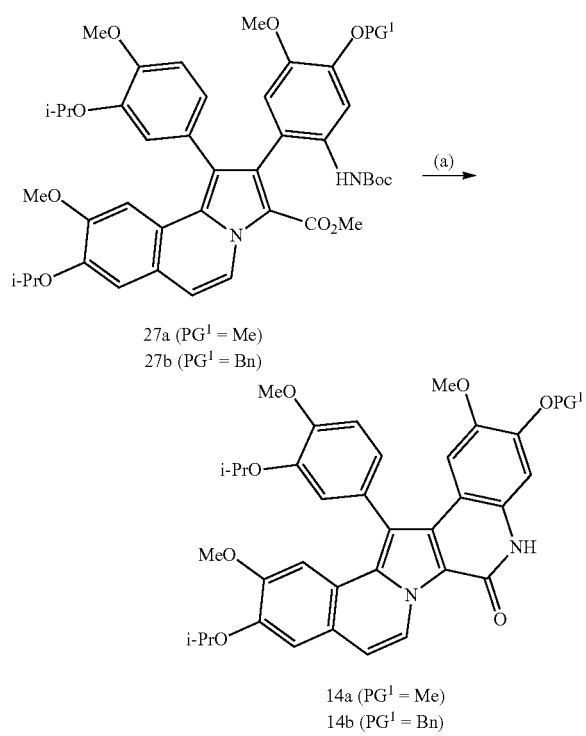

27a (PG¹ = Me)
27b (PG¹ = Bn)

14a (PG¹ = Me)
14b (PG¹ = Bn)

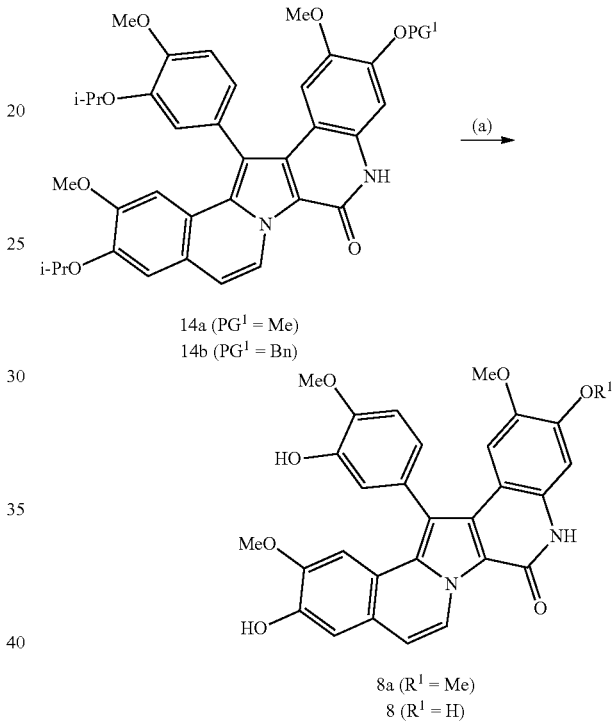

14a (PG¹ = Me)
14b (PG¹ = Bn)

8a (R¹ = Me)
8 (R¹ = H)

Step (a): Synthesis of Compound 14a

Under an argon atmosphere, to a solution of compound 27a (50.0 mg, 68.6 μmol) in tetrahydrofuran (3.0 mL) was added dropwise a tetrahydrofuran solution of tetrabutylammonium fluoride (1.0 M, 343 μL, 0.343 mmol) and the mixture was stirred in a sealed tube with heating at 85° C. for 19 hr. After allowing to cool, water was added and the solvent was evaporated. The precipitated solid was collected by suction filtration, and the obtained solid was washed successively with water and methanol and vacuum dried to give compound 14a as a pale-brown solid (33.6 mg). yield 82%.

¹H NMR (500 MHz, CDCl₃): δ 1.35 (d, J=6.1 Hz, 6H), 1.43 (d, J=6.1 Hz, 6H), 3.45 (s, 3H), 3.47 (s, 3H), 3.96 (s, 3H), 3.99 (s, 3H), 4.54 (sep, J=6.1 Hz, 1H), 4.69 (sep, J=6.1 Hz, 1H), 6.90 (s, 1H), 6.94 (d, J=7.4 Hz, 1H), 6.94 (s, 1H), 7.10 (s, 1H), 7.16 (d, J=8.1 Hz, 1H), 7.17 (d, J=1.7 Hz, 1H), 7.20 (s, 1H), 7.22 (dd, J=1.7 and 8.1 Hz, 1H), 9.59 (d, J=7.4 Hz, 1H), 10.588 (s, 1H).

HRDARTMS m/z. Calcd for $C_{35}H_{37}N_2O_7[(M+H)^+]$: 597.2601. Found: 597.2612.

Step (a): Synthesis of Compound 8a

Under an argon atmosphere, to a solution of compound 14a (20.0 mg, 33.5 μmol) in dry dichloromethane (12 mL) was added dropwise a heptane solution of boron trichloride (1.0 M, 235 μL, 0.235 mmol) at −78° C., and the mixture was stirred at the same temperature for 30 min. Thereafter, the mixture was allowed to warm to room temperature and stirred at the same temperature for 3 hr. To the reaction solution was added saturated aqueous sodium hydrogen carbonate solution, and the solvent was evaporated under reduced pressure. The precipitated solid was collected by suction filtration and the obtained solid was washed with water and vacuum dried. The obtained solid was purified by silica gel column chromatography (acetone) to give compound 8a as a pale-brown solid (14.2 mg). yield 71%.

¹H NMR (500 MHz, DMSO-d₆): δ 3.34 (s, 3H), 3.39 (s, 3H), 3.78 (s, 3H), 3.86 (s, 3H), 6.87 (s, 1H), 6.98-7.02 (m, 3H), 7.04 (d, J=7.4 Hz, 1H), 7.14 (s, 1H), 7.16 (s, 1H), 7.23 (d, J=8.7 Hz, 1H), 9.34 (s, 1H), 9.38 (d, J=7.4 Hz, 1H), 9.73 (br s, 1H), 11.34 (s, 1H).

HRFABMS m/z. Calcd for $C_{29}H_{25}N_2O_7[(M+H)^+]$: 513.1662. Found: 513.1676.

Step (a): Synthesis of Compound 8

According to the procedure described for the synthesis of compound 8a, compound 14b (30.0 mg, 44.6 µmol) and a heptane solution of boron trichloride (1.0 M, 445 µL, 0.445 mmol) were reacted. The obtained crude solid was purified by silica gel column chromatography (acetone) to give compound 8 as a pale-brown solid (18.6 mg). yield 84%.

$^1$H NMR (500 MHz, CDCl$_3$): δ 3.36 (s, 3H), 3.39 (s, 3H), 3.86 (s, 3H), 6.84 (s, 1H), 6.89 (s, 1H), 6.98-7.03 (m, 3H), 7.13 (s, 1H), 7.15 (s, 1H), 7.23 (d, J=8.2 Hz, 1H), 9.33 (s, 1H), 9.37 (d, J=7.4 Hz, 1H), 9.49 (s, 1H), 9.71 (s, 1H), 11.27 (s, 1H).

HRDARTMS m/z. Calcd for C$_{28}$H$_{23}$N$_2$O$_7$[(M+H)$^+$]: 499.1505. Found: 499.1502.

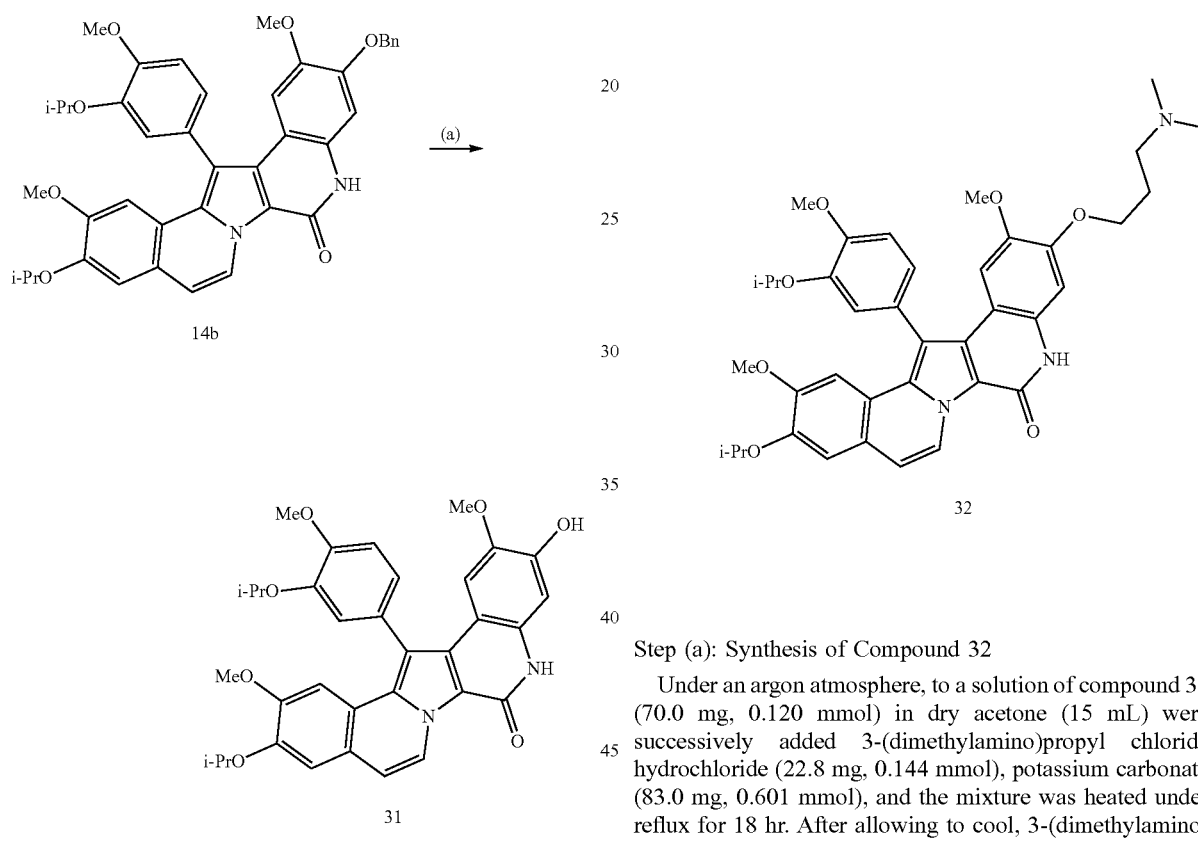

Step (a): Synthesis of Compound 31

Under an argon atmosphere, to a solution of compound 14b (300 mg, 0.446 mmol) in ethyl acetate (45 mL) and ethanol (45 mL) were successively added palladium carbon (Pd: 10%, 60.0 mg) and ammonium formate (844 mg, 13.4 mmol) and the mixture was heated under reflux for 30 min. After allowing to cool, the reaction mixture was filtered through celite. The filtrate was concentrated, and the residue was purified by silica gel column chromatography (acetone) to give compound 31 as a pale-yellow solid (258 mg). yield 99%.

$^1$H NMR (300 MHz, CDCl$_3$): δ 1.35 (d, J=6.1 Hz, 3H), 1.36 (d, J=6.1 Hz, 3H), 1.43 (d, J=6.1 Hz, 6H), 3.44 (s, 3H), 3.50 (s, 3H), 3.97 (s, 3H), 4.55 (sep, J=6.1 Hz, 1H), 4.69 (sep, J=6.1 Hz, 1H), 5.84 (br s, 1H), 6.87 (s, 2H), 6.94 (d, J=7.4 Hz, 1H), 7.09 (s, 1H), 7.14-7.24 (m, 4H), 9.34 (br s, 1H), 9.53 (d, J=7.4 Hz, 1H).

Step (a): Synthesis of Compound 32

Under an argon atmosphere, to a solution of compound 31 (70.0 mg, 0.120 mmol) in dry acetone (15 mL) were successively added 3-(dimethylamino)propyl chloride hydrochloride (22.8 mg, 0.144 mmol), potassium carbonate (83.0 mg, 0.601 mmol), and the mixture was heated under reflux for 18 hr. After allowing to cool, 3-(dimethylamino) propyl chloride hydrochloride (22.8 mg, 0.144 mmol) and potassium carbonate (83.0 mg, 0.601 mmol) were added, and the mixture was further heated under reflux for 5 hr. After allowing to cool, the mixture was diluted with acetone and filtered through celite. The filtrate was concentrated under reduced pressure and the residue was purified by CHROMATOREX Diol column chromatography (ethyl acetate-dichloromethane:methanol=10:1) and CHROMATOREX to give compound 32 as a pale-yellow solid (39.7 mg). yield 50%.

$^1$H NMR (500 MHz, CDCl$_3$): δ 1.34 (d, J=6.1 Hz, 6H), 1.43 (d, J=6.1 Hz, 6H), 2.08 (quin, J=6.9 Hz, 2H), 2.28 (s, 6H), 2.51 (t, J=7.2 Hz, 2H), 3.45 (s, 6H), 3.96 (s, 3H), 4.17 (t, J=6.7 Hz, 2H), 4.54 (sep, J=6.1 Hz, 1H), 4.68 (sep, J=6.1 Hz, 1H), 6.88 (s, 1H), 6.93 (d, J=7.4 Hz, 1H), 7.00 (s, 1H), 7.09 (s, 1H), 7.14 (d, J=8.2 Hz, 1H), 7.16 (d, J=1.7 Hz, 1H), 7.19 (s, 1H), 7.21 (dd, J=1.7 and 8.2 Hz, 1H), 9.59 (d, J=7.4 Hz, 1H), 10.58 (br s, 1H).

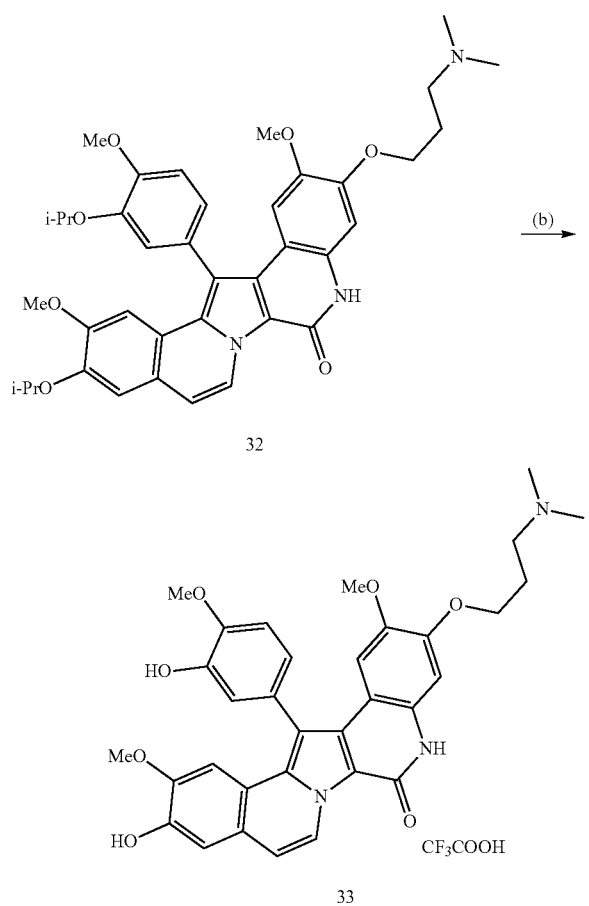

Step (b): Synthesis of Compound 33

Under an argon atmosphere, to a solution of compound 32 (15.2 mg, 22.8 μmol) in dry dichloromethane (5.0 mL) was added dropwise a nitrobenzene solution of aluminum chloride (1.0 M, 145 μL, 0.145 mmol) at room temperature, and the mixture was stirred at the same temperature for 72 hr. To the reaction solution was added a mixed solution of sodium hydrogen carbonate (36.7 mg, 0.437 mmol) and Rochelle salt (123 mg, 0.437 mmol) in water (2.1 mL). After vigorously stirring for 1 hr, dichloromethane and water were evaporated under reduced pressure. Water was added to the residue, nitrobenzene was removed azeotropically under reduced pressure, and the residue was dried under reduced pressure. To the residue were added dichloromethane (1.0 mL) and trifluoroacetic acid (1.0 mL) and the solvent was evaporated under reduced pressure. The residue was purified by column chromatography (Sephadex LH-20, 0.1% v/v trifluoroacetic acid-containing water—0.1% v/v trifluoroacetic acid-containing water:methanol=1:1–0.1% v/v trifluoroacetic acid-containing methanol) to give compound 33 as a brown solid (15.8 mg). yield 100%.

$^1$H NMR (500 MHz, DMSO-$d_6$): δ 2.11-2.18 (m, 2H), 2.82 (s, 3H), 2.83 (s, 3H), 3.20-3.26 (m, 2H), 3.36 (s, 3H), 3.39 (s, 3H), 3.86 (s, 3H), 4.05 (t, J=5.9 Hz, 2H), 6.90 (s, 1H), 6.98-7.02 (m, 3H), 7.05 (d, J=7.5 Hz, 1H), 7.14 (s, 1H), 7.16 (s, 1H), 7.23 (d, J=8.7 Hz, 1H), 9.37 (d, J=7.5 Hz, 1H), 9.60 (br s, 1H), 9.75 (br s, 2H), 11.37 (br s, 1H).

Experimental Example 1 Evaluation of Proliferation Inhibitory Activity Using EGFR Gene-Transfected BaF3 Cells The activity at the enzyme level of a drug is not necessarily directly linked to the activity at the cellular level due to such reasons as the cell membrane permeability of the drug or off-target inhibition. Thus, evaluation of EGFR inhibitory activity using transfected BaF3 cells, which has been established as an evaluation method of kinase inhibitors at a cell level, was performed. BaF3 cells (mouse prolymphocytic cells) can proliferate only in the presence of IL-3 (Interleukin-3). On the other hand, BaF3 cells transfected with EGFR gene can proliferate in an EGFR-dependent manner even in the absence of IL-3. When an EGFR inhibitor is added, BaF3 cells cannot proliferate; however, when IL-3 is added, they can proliferate even in the presence of an EGFR inhibitor. Utilizing such properties, the activity and specificity of an EGFR inhibitor can be evaluated.

This time, the proliferation inhibitory activity of lamellarins (compound 26a, 26b, 26c, 26d) and azalamellarins (compound 8, 8a, 33) was evaluated in BaF3 transfected with a doubly mutated EGFR gene (L858R/T790 M), BaF3 transfected with a doubly mutated EGFR gene (del exon19/T790 M) and BaF3 transfected with a triply mutated EGFR gene (L858R/T790 M/C797S), BaF3 transfected with a triply mutated EGFR gene (del exon19/T790 M/C797S). As the positive controls, the first-generation inhibitor gefitinib, second-generation inhibitor afatinib and third-generation inhibitor osimertinib were used. The specific test method is as follows.

2 μg of various pBABE-EGFR plasmids were introduced into BaF3 cells (2×10$^6$ cells) by using the NEON electroporation system (Thermo Fisher Scientific, Inc.) and the cells were cultured in RPMI-1640 medium supplemented with 10 ng/mL IL-3, 100 U/mL penicillin, 100 μg/mL streptomycin and 10% fetal bovine serum under 5% carbon dioxide/95% air atmosphere at 37° C. Two days later, 1 μg/mL puromycin was added, and the cells were cultured for 4 days. The cells were washed with PBS, cultured in IL-3-free medium to obtain cells that proliferate IL-3 independently. The cells were seeded in a 96-well microplate (Thermo Fisher Scientific, Inc.) at 3000 cells/well, various concentrations of the test compound were added, and the cells were cultured in 150 μL of the medium for 4 days. 15 μL of 5 mg/mL MTT (thiazolyl blue tetrazolium bromide) solution was added to each well, the cells were incubated at 37° C. for 4 hr, 100 μL of 20% SDS was added, and the cells were further incubated overnight. The absorbance at 570 nm was measured by a microplate reader (Beckman Coulter) and 50% inhibitory concentration (IC$_{50}$) of cell proliferation was calculated. The results are shown in the following Tables.

TABLE 1 proliferation inhibitory activity using EGFR (L858R/T790M) gene-transfected BaF3 cell

| compound | IC$_{50}$ (nM) | |
|---|---|---|
| | −IL-3 | +IL-3 |
| compound 26a | 4.50 | 4.51 |
| compound 26c | 0.32 | 0.50 |
| compound 26d | 0.81 | 0.97 |
| compound 26b | 0.96 | 3.05 |
| compound 8 | 0.0093 | 0.037 |
| compound 8a | 0.0076 | 0.011 |
| compound 33 | 0.046 | 0.18 |

TABLE 1-continued proliferation inhibitory activity using EGFR
(L858R/T790M) gene-transfected BaF3 cell

| | IC$_{50}$ (nM) | |
|---|---|---|
| compound | −IL-3 | +IL-3 |
| gefitinib | >10 | >10 |
| afatinib | 0.29 | 4.56 |
| osimertinib | 0.0077 | 4.54 |

TABLE 2 proliferation inhibitory activity using EGFR
(del exon19/T790M) gene-transfected BaF3 cell

| | IC$_{50}$ (nM) | |
|---|---|---|
| compound | −IL-3 | +IL-3 |
| compound 26a | 2.17 | 6.56 |
| compound 26c | 0.18 | 0.26 |
| compound 26d | 0.22 | 0.92 |
| compound 26b | 0.54 | 2.17 |
| compound 8 | — | — |
| compound 8a | — | — |
| compound 33 | — | — |
| gefitinib | 5.05 | >10 |
| afatinib | 0.17 | 4.56 |
| osimertinib | 0.0053 | 4.53 |

TABLE 3 proliferation inhibitory activity using EGFR (T790M/L858R/C797S)
gene-transfected BaF3 cell

| | IC$_{50}$ (nM) | |
|---|---|---|
| compound | −IL-3 | +IL-3 |
| compound 26a | 0.66 | 4.36 |
| compound 26c | 0.11 | 0.65 |
| compound 26d | 0.16 | 0.90 |
| compound 26b | 0.24 | 1.83 |
| compound 8 | 0.0067 | 0.032 |
| compound 8a | 0.0074 | 0.026 |
| compound 33 | 0.041 | 0.13 |
| gefitinib | 4.74 | 8.34 |
| afatinib | 0.97 | 1.85 |
| osimertinib | 0.78 | 4.32 |

TABLE 4 proliferation inhibitory activity using EGFR (del
exon19/T790M/C797S) gene transfected BaF3 cell

| | IC$_{50}$ (nM) | |
|---|---|---|
| compound | −IL-3 | +IL-3 |
| compound 26a | — | — |
| compound 26c | 0.14 | — |
| compound 26d | 0.23 | 0.99 |
| compound 26b | — | — |
| compound 8 | 0.0086 | 0.027 |
| compound 8a | 0.0074 | 0.0095 |
| compound 33 | 0.059 | 0.15 |
| gefitinib | 5.77 | >10 |
| afatinib | 0.95 | 4.19 |
| osimertinib | 0.93 | 4.56 |

Experimental Example 1 revealed the following.

(1) Lamellarins showed the same level of activity as that of afatinib, and azalamellarins showed activity comparable to that of osimertinib in BaF3 (L858R/T790M) expressing a double mutant EGFR. However, the both had a narrow therapeutic window (defined in this case to be the difference between −IL3 and +IL3), and superiority to afatinib or osimertinib was not found.

(2) Lamellarins showed the same level of activity as that of afatinib in BaF3 (del exon19/T790M) expressing a double mutant EGFR. However, the both had a narrow therapeutic window and superiority to afatinib or osimertinib was not found.

(3) On the other hand, the activities of afatinib and osimertinib were greatly attenuated in BaF3 (L858R/T790M/C797S) and BaF3 (del exon19/T790M/C797S) expressing triple mutant EGFRs (particularly osimertinib). However, such attenuation was not found in lamellarins and azalamellarins, which are reversible inhibitors, but rather, an improvement in the activity was observed. The activity exceeded that of afatinib and osimertinib. In addition, significant spread of the therapeutic window was observed in each compound, and involvement of EGFR inhibition in the inhibition of cell proliferation was clearly shown.

Experimental Example 2 Evaluation of Proliferation
Inhibitory Activity of Compound 26d in a
Wild-Type EGFR Gene-Transfected BaF3 Cell The selectivity of compound 26d for EGFR with an activating mutation was examined using BaF3 cells expressing wild-type EGFR without an activating mutation. 2 μg of pBABE-EGFR wild-type was introduced into BaF3 cells (2×10$^6$ cells) by using the NEON electroporation system (Thermo Fisher Scientific, Inc.), and the cells were cultured in RPMI-1640 medium containing 10 ng/mL IL-3, 100 U/mL penicillin, 100 μg/mL streptomycin and 10% fetal bovine serum under 5% carbon dioxide/95% air atmosphere at 37° C. Two days later, 1 μg/mL puromycin was added and resistant cells were selected. The cells were washed twice with PBS, seeded in a 96 well microplate (Thermo Fisher Scientific, Inc.) at 30000 cells/well, 10 ng/mL EGF or IL-3 and various concentrations of compound 26d were added and the cells were cultured in 150 μL of the medium for 4 days. 15 μL of 5 mg/mL MTT (thiazolyl blue tetrazolium bromide) solution was added to the well, the cells were incubated at 37° C. for 4 hr, 100 μL of 20% SDS was added, and the cells were further incubated overnight. The absorbance at 570 nm was measured by a microplate reader (Beckman Coulter) and 50% inhibitory concentration (IC$_{50}$) of cell proliferation was calculated. The results are shown in the following Table.

TABLE 5 proliferation inhibitory activity of compound
26d in wild-type EGFR gene-introduced BaF3 cell

| | IC$_{50}$ (nM) | |
|---|---|---|
| | −IL-3 | +IL-3 |
| EGFR WT | 519.82 | 901.66 |
| EGFR (del exon19/T790M/C797S) | 126.75 | 822.38 |

Compared to BaF3 (del exon19/T790 M/C797S) having activating mutation, BaF3 cells expressing wild-type EGFR showed a low effect of compound 26d which was of the same level as the proliferation inhibitory activity in the presence of IL-3. Therefore, it was shown that compound 26d is selective for EGFR with triple mutation.

Experimental Example 3 Evaluation of Proliferation Inhibitory Activity Using EGFR Gene-Transfected Lung Adenocarcinoma Cells The proliferation inhibitory activity of compound 26d in a lung adenocarcinoma cell line was examined. 2 µg of pBABE-EGFR was transfected into a lung adenocarcinoma cell line, PC-9, with an exon19 deletion (del exon19) in the EGFR gene by using Viafect transfection reagent (Promega KK.) and the cells were cultured in RPMI-1640 medium containing 100 U/mL penicillin, 100 µg/mL streptomycin and 10% fetal bovine serum under 5% carbon dioxide/95% air atmosphere at 37° C. Two days later, 2 µg/mL puromycin was added and resistant cells were selected. These cells and A549 cells expressing wild-type EGFR were seeded in a 96 well microplate (Thermo Fisher Scientific, Inc.) respectively at 3,000 cells/well and 7,500 cells/well, various concentrations of the test compound were added, and the cells were cultured in 150 µL of the medium for 4 days. 15 µL of 5 mg/mL MTT (thiazolyl blue tetrazolium bromide) solution was added to the well, the cells were incubated at 37° C. for 4 hr, 100 µL of 20% SDS was added, and the cells were further incubated overnight. The absorbance at 570 nm was measured by a microplate reader (Beckman Coulter) and 50% inhibitory concentration ($IC_{50}$) of cell proliferation was calculated. The results are shown in the following Table.

TABLE 6

Proliferation inhibitory activity of compound 26d in EGFR gene-transfected lung adenocarcinoma PC-9 cell and EGFR wild-type A549

| | $IC_{50}$ (nM) |
|---|---|
| PC-9 | 658.5 |
| del exon19/T790M | 493.9 |
| L858R/T790M | 719.0 |
| del exon19/T790M/C797S | 739.9 |
| L858R/T790M/C797S | 595.7 |
| A549 | 2861.7 |

EGFR genes with activating mutations were transfected into PC-9 and the proliferation inhibitory activity of compound 26d in a lung adenocarcinoma cell line was examined. As the result, compound 26d inhibited proliferation at almost the same level of concentration irrespective of the presence or absence of resistant mutations (T790M and C797S mutations).

Proliferation of a lung adenocarcinoma cell line, A549, expressing wild-type EGFR without a mutation was inhibited at a higher concentration than that for PC-9 cell with activating mutation. Therefore, it was shown that compound 26d is selective for EGFR with an activating mutation.

Experimental Example 4 Evaluation of Inhibition of EGFR Signal by Compound 26d

Figure 2:
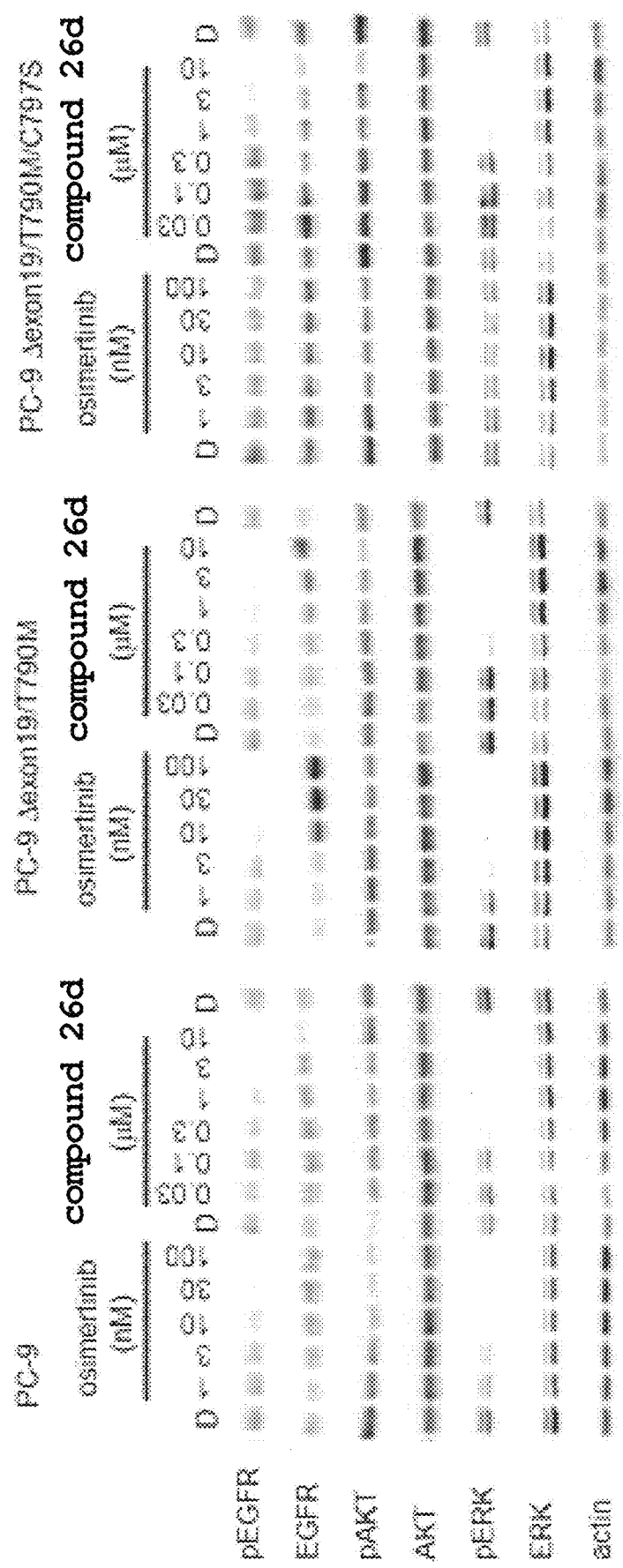
FIG. 2 shows inhibition of EGFR signal by compound 26d in Experimental Example 4.

An EGFR tyrosine kinase inhibitor inhibits autophosphorylation of EGFR and its downstream signalings. Thus, whether compound 26d inhibits autophosphorylation of EGFR (del exon19/T790 M/C797S) and the downstream signalings at a cellular level was examined. Lung adenocarcinoma PC-9 cells expressing EGFR (del exon19/T790M) or EGFR (del exon19/T790M/C797S) respectively were seeded in a 6 well plate at 100,000 cells/well, and the cells were cultured in RPMI-1640 medium supplemented with 100 µg/mL streptomycin and 10% fetal bovine serum under 5% carbon dioxide/95% air atmosphere at 37° C. The next day, osimertinib or compound 26d was added and the cells were cultured for 4 hr. After washing with ice-cooled PBS, the cells were suspended in 100 µL of RIPA buffer (20 mM Tris-HCL pH 7.5, 150 mM NaCl, 1% NP40, 1% sodium deoxycholate, 0.1% SDS) containing 5 mM sodium vanadate, 5 mM sodium fluoride, protease inhibitor cocktail (Roche K.K.), incubated on ice for 30 min and centrifuged at 15000 rpm for 30 min, and the supernatants were used as cell lysates. The cell lysates were separated by SDS polyacrylamide gel and transferred to PVDF membrane. The PVDF membrane was blocked with 5% skim milk for 30 min and applied to western blotting using anti-phosphorylated EGFR antibody, anti-EGFR antibody, anti-phosphorylated AKT antibody, anti-AKT antibody, anti-phosphorylated ERK antibody (Cell Signaling Technologies K.K.), anti-ERK antibody (Santa Cruz), anti-actin antibody (Sigma), horseradish peroxidase-conjugated anti-mouse IgG or horseradish peroxidase-conjugated anti-rabbit IgG. For detection, ECL Prime Detection Reagent and LAS3000 (GE Healthcare Corporation) were used. The results are shown in FIG. 2.

Compound 26d suppressed phosphorylation of EGFR and phosphorylation of ERK in the downstream of EGFR signal in PC-9 cells. On the other hand, suppression of phosphorylation of AKT in the downstream of EGFR signal was not obvious. Phosphorylation of these proteins was suppressed at almost the same level of concentration irrespective of the presence or absence of the resistant mutant (T790M, C797S mutation). Therefore, it was shown that compound 26d suppresses the EGFR signaling in cells existing drug-resistant EGFR mutant.

Figure 3:
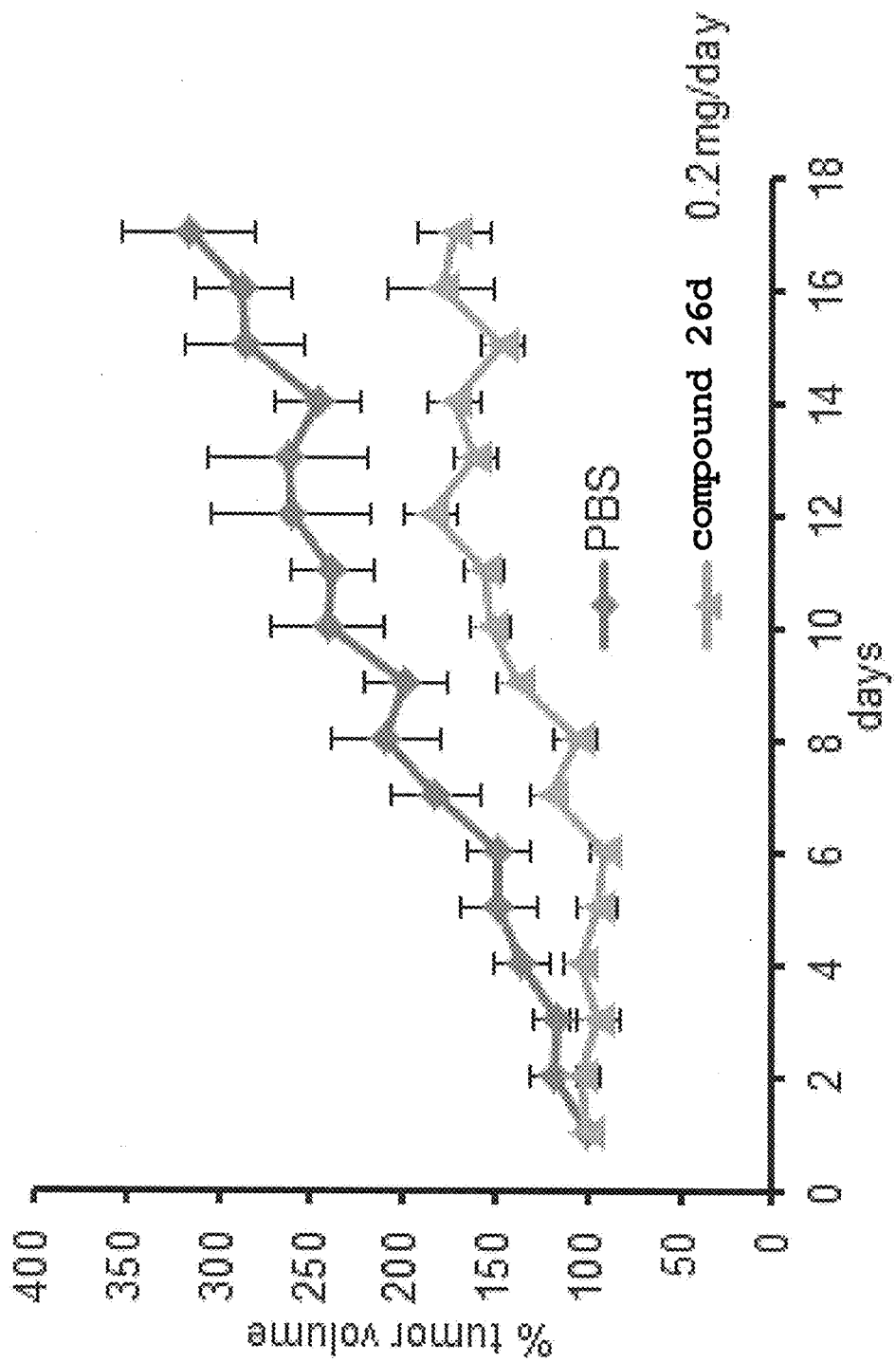
FIG. 3 shows an antitumor effect of compound 26d in a mouse xenograft model in Experimental Example 5.
Figure 4:
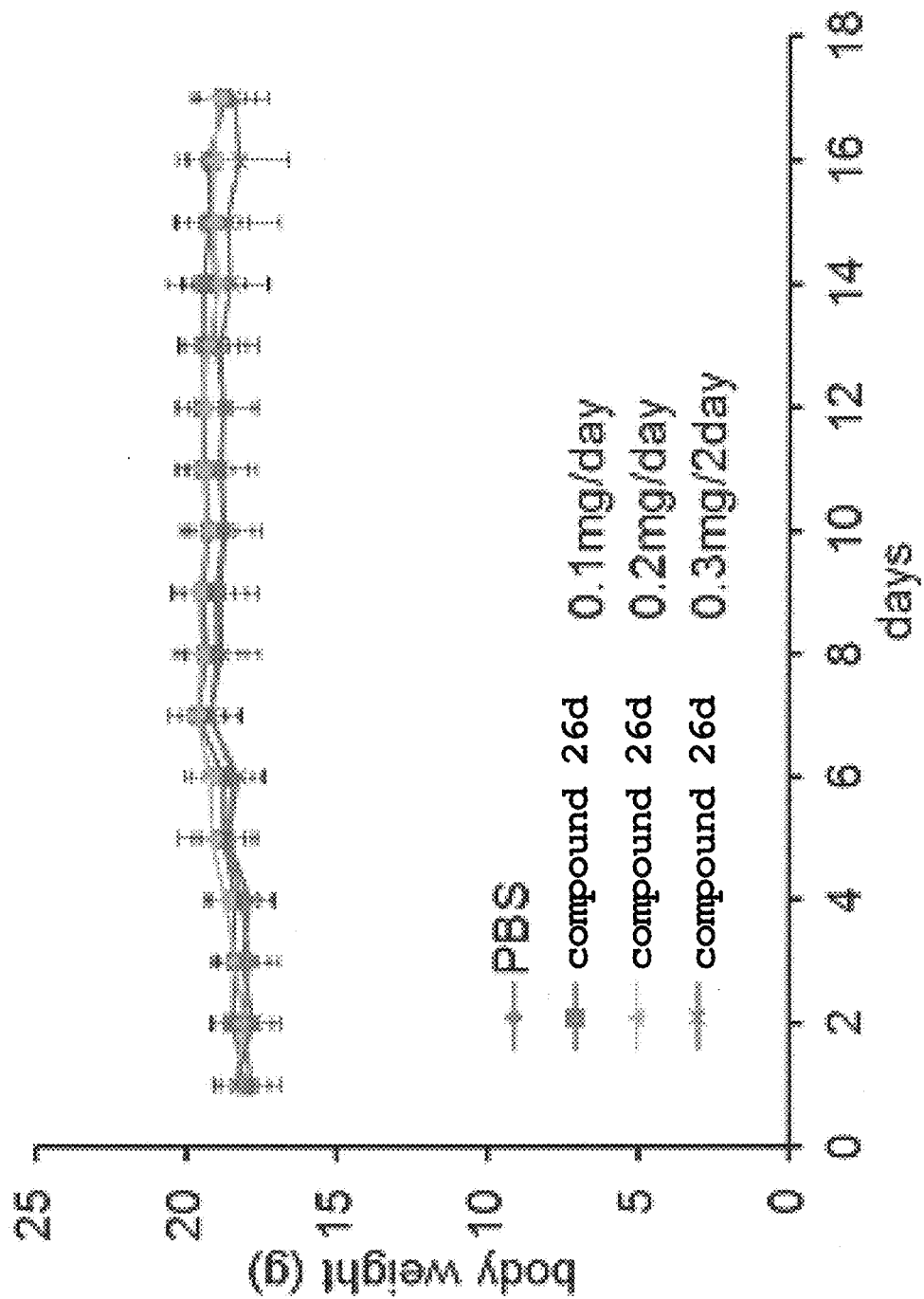
FIG. 4 shows the transition of body weight of nude mice during the administration period of compound 26d in Experimental Example 5.

Experimental Example 5 Evaluation of an Antitumor Effect of Compound 26d in a Mouse Zenograft Model The therapeutic effect of compound 26d at the animal level was examined using a mouse zenograft model. PC-9 cells expressing EGFR (del exon19/T790M/C797S) were prepared at $5\times10^7$ cells and mixed with Matrigel (Becton Dickinson Company, LTD.) at 1:1 ratio. These were subcutaneously injected by 100 µL into Balb/c nude mouse (CHARLES RIVER LABORATORIES JAPAN, INC.) After tumor formation was verified, compound 26d (0.2 mg) was intraperitoneally administered every day and the tumor diameters were measured. The tumor volume was calculated by the major axis (mm)×the minor axis $(mm)^2/2$. The results are shown in FIGS. 3 and 4.

Compound 26d suppressed the tumor enlargement of PC-9 cells expressing EGFR (del exon19/T790M/C797S) gene subcutaneously transplanted into nude mice. Therefore, it was shown that, at the animal level, compound 26d suppresses an enlargement of a human lung cancer graft that acquired resistance to gefitinib and osimertinib. During the treatment period, body weight loss was not observed. Thus, compound 26d is considered to not cause remarkable toxicity.

As described above, the compound of the present invention created based on a structure-based drug design has been clarified to strongly inhibit EGFR (L858R/T790M/C797S) and EGFR (del exon19/T790M/C797S) at the cell level. The activity thereof is strikingly stronger than existing approved EGFR-TKI (gefitinib, afatinib, and osimeltinib), and the compound is considered to be useful as a lead compound for the development of a therapeutic drug for non-small cell lung cancer with triply mutated EGFR (the fourth-generation EGFR-TKI), for which no treatment method exists at this moment.

INDUSTRIAL APPLICABILITY

The compound of the present invention has a tyrosine kinase inhibitory activity specific to C797S resistant mutant EGFR (particularly C797S tertiary-resistant mutant EGFR) and is useful as a C797S mutant resistant EGFR (particularly C797S tertiary-resistant mutant EGFR) tyrosine kinase inhibitor, an agent for preventing and/or treating non-small cell lung cancer with resistance mutant EGFR and the like, and the like.

This application is based on patent application No. 2017-064866 filed in Japan, the contents of which are encompassed in full herein.

The invention claimed is:

1. A compound represented by the formula (I):

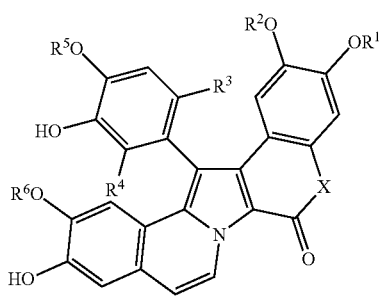

wherein
X is O or NH,
R$^1$ and R$^2$ are each independently a hydrogen atom or an amino substituted hydrocarbon group, wherein the amino group is optionally mono- or di-substituted by C$_{1-6}$alkyl group or guanidino group,
R$^3$ and R$^4$ are each a hydrogen atom, and
R$^5$ and R$^6$ are each independently a hydrocarbon group, excluding the following compound:

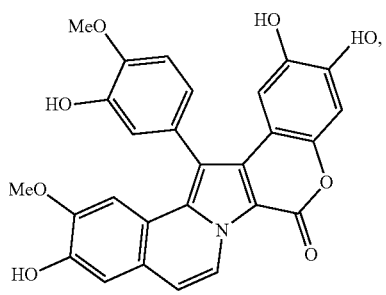 [SMILES: COc1ccc(-c2c3c4cc(O)c(O)cc4oc(=O)c3n3ccc4cc(O)c(OC)cc4c23)cc1O]

or a salt thereof.

2. A method for inhibiting C797S resistant mutant EGFR tyrosine kinase activity, the method comprising contacting a cell expressing C797S resistant mutant EGFR with a compound or salt of claim 1.

3. A method for treating non-small cell lung cancer in a subject in need thereof, the method comprising administering to the subject a compound or salt of claim 1.

4. The method of claim 3, wherein the non-small cell lung cancer is associated with C797S resistant mutant EGFR.

5. The compound of claim 1, wherein the compound of formula (I) is

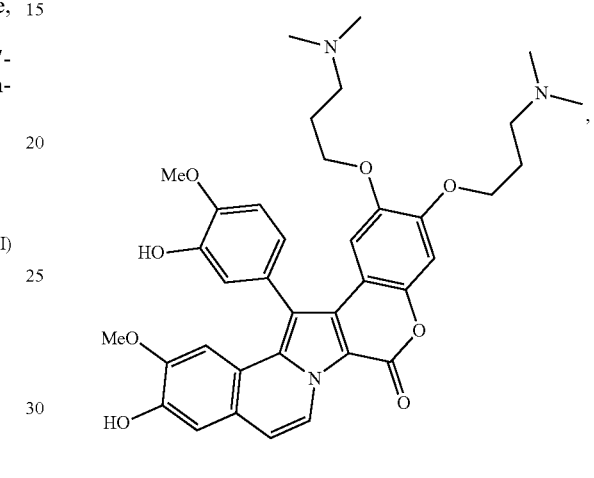

or a salt thereof.

6. The compound of claim 1, wherein the compound of formula (I) is

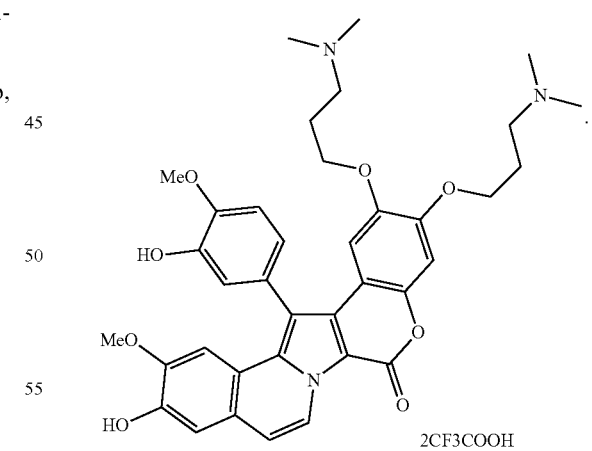

* * * * *